United States Patent
Fu et al.

(10) Patent No.: US 10,525,034 B2
(45) Date of Patent: Jan. 7, 2020

(54) SUNITINIB FORMULATIONS AND METHODS FOR USE THEREOF IN TREATMENT OF GLAUCOMA

(71) Applicant: The Johns Hopkins University, Baltimore, MD (US)

(72) Inventors: Jie Fu, Baltimore, MD (US); Justin Hanes, Baltimore, MD (US); Donald Jeffrey Zack, Baltimore, MD (US); Zhiyong Yang, San Diego, CA (US); Derek Stuart Welsbie, Lutherville, MD (US); Cynthia Ann Berlinicke, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/536,272

(22) PCT Filed: Dec. 15, 2015

(86) PCT No.: PCT/US2015/065878
§ 371 (c)(1),
(2) Date: Jun. 15, 2017

(87) PCT Pub. No.: WO2016/100380
PCT Pub. Date: Jun. 23, 2016

(65) Prior Publication Data
US 2017/0360750 A1 Dec. 21, 2017

Related U.S. Application Data

(60) Provisional application No. 62/092,118, filed on Dec. 15, 2014, provisional application No. 62/139,306, filed on Mar. 27, 2015.

(51) Int. Cl.
| | | |
|---|---|---|
| *A61K 31/404* | (2006.01) | |
| *A61K 9/00* | (2006.01) | |
| *A61K 9/16* | (2006.01) | |
| *A61K 9/19* | (2006.01) | |
| *A61K 31/506* | (2006.01) | |
| *A61K 9/51* | (2006.01) | |

(52) U.S. Cl.
CPC .......... *A61K 31/404* (2013.01); *A61K 9/0051* (2013.01); *A61K 9/1647* (2013.01); *A61K 9/19* (2013.01); *A61K 9/5153* (2013.01); *A61K 9/5192* (2013.01); *A61K 31/506* (2013.01)

(58) Field of Classification Search
CPC .................................................. A61K 31/404
USPC ........................................................ 514/414
See application file for complete search history.

(56) References Cited

U.S. PATENT DOCUMENTS 3,266,987 A 8/1966 Palmer
4,460,563 A 7/1984 Calanchi
4,794,000 A 12/1988 Ecanow
4,911,920 A 3/1990 Jani et al.
4,997,652 A 3/1991 Wong
5,013,556 A 5/1991 Woodle et al.
5,019,400 A 5/1991 Gombotz et al.
5,441,722 A 8/1995 Eng
5,624,677 A 4/1997 El-Rashidy et al.
5,869,103 A 2/1999 Yeh et al.
6,007,845 A 12/1999 Domb et al.
6,201,072 B1 3/2001 Rathi et al.
6,287,588 B1 9/2001 Shih et al.
6,495,164 B1 12/2002 Ramstack et al.
6,566,406 B1 5/2003 Pathak
6,589,549 B2 7/2003 Shih et al.
6,632,457 B1 10/2003 Sawhney
6,703,047 B2 3/2004 Sawhney
6,706,289 B2 3/2004 Lewis et al.
6,818,018 B1 11/2004 Sawhney
6,841,617 B2 1/2005 Jeong et al.
7,501,179 B2 3/2009 Song et al.
8,252,307 B2 8/2012 Ashton
8,277,830 B2 10/2012 de Jean, Jr. et al.
8,298,578 B2 10/2012 de Jean, Jr. et al.
8,399,006 B2 3/2013 de Jean, Jr. et al.

(Continued)

FOREIGN PATENT DOCUMENTS

EP 3006050 4/2016
GB 929401 6/1963

(Continued)

OTHER PUBLICATIONS

Patel et al., J. Med. Chem, 2017, 60(19): 8083-8102 (abstract only).*
Hara et al. Cardiovasc Drug Rev, 2005, 23(1): 43-56.*
Hara et al. Cardiovasc Drug Rev, 2004, 22(3): 199-214.*
Suenaga et al., Cell Tissue Res, 2006, 325(1): 189-95.*
Robitaille et al., Cell Death Differ, 2008, 15(9): 1522-31.*
Amparo, et al., "Safety and efficacy of the multitargeted receptor kinase inhibitor pazopanib in the treatment of corneal neovascularization", Invest Ophthalmol Vis Sci, 54(1):537-44 (2013).
Anderson and Shire, "Biodegradation and biocompatibility of PLA and PLGA microspheres", Adv Drug Deliv Rev, 28(1):5-24 (1997).
Bressler, "Age-related macular degeneration is the leading cause of blindness", JAMA, 291:1900-01(2004).

(Continued)

*Primary Examiner* — Rei Tsang Shiao
(74) *Attorney, Agent, or Firm* — Pabst Patent Group LLP

(57) ABSTRACT

Methods for increasing the encapsulation or incorporation of Sunitinib into polymeric matrices have been developed. The resulting formulations provide for more sustained controlled release of sunitinib or other inhibitors of JNK signaling, which bind to DLK. Increased loading is achieved using an alkaline solvent system. The pharmaceutical compositions can be administered to treat or reduce neuronal death due to elevated intraocular pressure. Upon administration, the sunitinib or other inhibitor is released over an extended period of time at concentrations which are high enough to produce therapeutic benefit, but low enough to avoid unacceptable levels of cytotoxicity, and which provide much longer release than inhibitor without conjugate.

14 Claims, 9 Drawing Sheets

Specification includes a Sequence Listing.

(56) References Cited

U.S. PATENT DOCUMENTS

| | | | |
|---|---|---|---|
| 8,409,606 B2 | 4/2013 | Sawhney | |
| 8,409,607 B2 | 4/2013 | Hughes et al. | |
| 8,492,334 B2 | 7/2013 | Lavik et al. | |
| 8,628,801 B2 | 1/2014 | Garreta et al. | |
| 8,632,809 B2 | 1/2014 | Asgharian et al. | |
| 8,663,674 B2 | 3/2014 | Wen et al. | |
| 8,685,435 B2 | 4/2014 | Nivaggioli et al. | |
| 8,889,193 B2 | 11/2014 | McDonnell | |
| 8,957,034 B2 | 2/2015 | Hanes et al. | |
| 8,962,577 B2 | 2/2015 | Hanes et al. | |
| 8,993,615 B2 * | 3/2015 | Zack | A61K 31/00 514/414 |
| 9,056,057 B2 | 6/2015 | Popov et al. | |
| 9,095,506 B2 | 8/2015 | Spanda et al. | |
| 9,114,070 B2 | 8/2015 | Hara et al. | |
| 9,125,807 B2 | 9/2015 | Sawhney | |
| 9,162,981 B2 | 10/2015 | Zack et al. | |
| 9,205,150 B2 | 12/2015 | Jarrett | |
| 9,327,037 B2 | 5/2016 | Suk et al. | |
| 9,382,229 B2 | 7/2016 | Zack et al. | |
| 9,415,020 B2 | 8/2016 | Ensign et al. | |
| 9,533,068 B2 | 1/2017 | Kashiwabuchi et al. | |
| 9,655,882 B2 * | 5/2017 | Zack | A61K 31/404 |
| 9,775,906 B2 | 10/2017 | Sawhney | |
| 2004/0175429 A1 | 9/2004 | Alavattam | |
| 2004/0234611 A1 | 11/2004 | Ahlheim et al. | |
| 2004/0258763 A1 | 12/2004 | Bell | |
| 2005/0048123 A1 | 3/2005 | Su et al. | |
| 2005/0244472 A1 | 11/2005 | Hughes | |
| 2006/0263335 A1 | 11/2006 | France | |
| 2007/0149593 A1 | 6/2007 | Ghosh et al. | |
| 2008/0166411 A1 | 6/2008 | Shah et al. | |
| 2008/0187568 A1 | 8/2008 | Sawhney | |
| 2008/0241248 A1 | 10/2008 | France | |
| 2008/0305172 A1 | 12/2008 | Ahlheim et al. | |
| 2009/0203709 A1 | 8/2009 | Steinberg et al. | |
| 2010/0063135 A1 | 3/2010 | Dande et al. | |
| 2010/0063175 A1 | 3/2010 | Ginty et al. | |
| 2010/0074957 A1 | 3/2010 | Robinson et al. | |
| 2010/0124565 A1 | 5/2010 | Spada | |
| 2010/0215580 A1 | 8/2010 | Hanes et al. | |
| 2010/0227905 A1 | 9/2010 | Kabra et al. | |
| 2010/0247669 A1 | 9/2010 | Eliasof et al. | |
| 2011/0142936 A1 | 6/2011 | Campbell | |
| 2012/0052041 A1 | 3/2012 | Basu et al. | |
| 2012/0063997 A1 | 3/2012 | Hunter | |
| 2012/0071865 A1 | 3/2012 | Jarrett | |
| 2012/0121718 A1 | 5/2012 | Lai et al. | |
| 2012/0269894 A1 | 10/2012 | Ahlheim et al. | |
| 2012/0321719 A1 * | 12/2012 | McDonnell | A61K 9/0051 424/497 |
| 2013/0071349 A1 | 3/2013 | Robinston et al. | |
| 2013/0071462 A1 | 3/2013 | Jarrett | |
| 2013/0122064 A1 | 5/2013 | Ahlheim et al. | |
| 2013/0183244 A1 | 7/2013 | Hanes et al. | |
| 2013/0272994 A1 | 10/2013 | Fu et al. | |
| 2013/0316001 A1 | 11/2013 | Popov et al. | |
| 2013/0316006 A1 | 11/2013 | Popov | |
| 2014/0107025 A1 | 4/2014 | Wirostko | |
| 2014/0294986 A1 | 10/2014 | Liu et al. | |
| 2014/0329913 A1 | 11/2014 | Hanes et al. | |
| 2015/0086484 A1 | 3/2015 | Hanes et al. | |
| 2015/0099805 A1 | 4/2015 | Hughes | |
| 2015/0147406 A1 | 5/2015 | Robinson et al. | |
| 2015/0157562 A1 | 6/2015 | Hughes | |
| 2016/0106587 A1 | 4/2016 | Jarrett | |
| 2016/0166504 A1 | 6/2016 | Jarrett | |
| 2016/0310417 A1 | 10/2016 | Prausnitz et al. | |
| 2016/0324836 A1 | 11/2016 | Aston et al. | |
| 2016/0331738 A1 | 11/2016 | Jarrett | |
| 2017/0020729 A1 | 1/2017 | Jarrett | |
| 2017/0143636 A1 | 5/2017 | Jarrett | |
| 2017/0157147 A1 | 6/2017 | Hanes et al. | |
| 2017/0027301 A1 | 9/2017 | Fu et al. | |
| 2018/0008718 A1 | 1/2018 | Fu et al. | |
| 2018/0333282 A1 | 11/2018 | Sawhney | |

FOREIGN PATENT DOCUMENTS

| | | |
|---|---|---|
| GB | 929406 | 6/1963 |
| JP | 2016132616 | 7/2016 |
| KR | 20150117745 | 10/2015 |
| WO | 2008041001 | 4/2008 |
| WO | 2008093094 | 8/2008 |
| WO | 2008093095 | 8/2008 |
| WO | 2010079496 | 7/2010 |
| WO | 2010100506 | 9/2010 |
| WO | WO2011/119777 | * 9/2011 |
| WO | WO2012112674 | * 8/2012 |
| WO | 2013177367 | 11/2013 |
| WO | WO2013/177367 | * 11/2013 |

OTHER PUBLICATIONS

Cakmak, et al., "The effects of topical everolimus and sunitinib on corneal neovascularization", Cutan Ocul Toxicol, 35(2):. 97-103 (2015).

D'Amico, "Diseases of the Retina", N. Engl. J. Med., 331:95-106 (1994).

Fuchs, et al., Sunitinib-eluting beads for chemoembolization: methods for in vitro evaluation of drug relaease, Intl J Pharma., 482(1-2):68-74 (2014).

Gaudana, et al., "Recent perspectives in ocular drug delivery", Pharm Res, 26(5):1197-216 (2009).

Govindarajan and Gipson, Membrane-tethered mucins have multiple functions on the ocular surface, Exp Eye Res, 90(6): p. 655-63 (2010).

Herrero-Vanrell, et al., "The potential of using biodegradable microspheres in retinal diseases and other intraocular pathologies", Prog Retinal Eye Res., 42:27-43 (2014).

International Search Report for corresponding PCT application PCT/US2015/065878 dated Apr. 1, 2016.

Ko, et al., "Inhibition of corneal neovascularization by subconjunctival and topical bevacizumab and sunitinib in a rabbit model.", Cornea, 32(5):689-95 (2013).

Li, et al., "Microencapsulation by solvent evaporation: state of the art for process engineering approaches", Intl J Pharmaceutics, 363(1-2):26-39 (2008).

Makadia and Siegel, "Poly Lactic-co-Glycolic Acid (PLGA) as Biodegradable Controlled Drug Delivery Carrier", Polymers (Basel), 3(3):1377-97 (2011).

Perez-Santonja, et al., "Vascular morphological and microdensity changes of corneal neovascularization induced by topical bevacizumab and sunitinib in an animal model", Arch Soc Esp Oftalmol, 88(12):473-81 (2013).

Ramazani, et al., "Sunitinib microspheres based on [PDLL-PEG-PDLA]-b-PLLA multi-block copolymers for ocular drug delivery", Eur J Pharm Biopharma., 95(19):368-77 (2015).

Tobe, et al., "Targeted disruption of the FGF2 gene does not prevent choroidal neovascularization in a murine model", Am. J. Pathol., 135(5):1641-6(1998).

Weisbie, et al., "functional genomic screening identifies dual leucine zipper kinased as a key mediator of retinal ganglion cell death", PNAS, 110(10):4045-50 (2013).

Zhao, et sl., "Preparation and Characterization of sunitinib-loaded microspheres for arterial embolization", J Chinese Pharma., 23(8):1003-57 (2014).

Ayalasomayajula, S.P. and Kompella, U.B., "Subconjunctivally administered celecoxib-PLGA microparticles sustain retinal drug levels and alleviate diabetes-induced oxidative stress in a rat model", Eur. J. Pharm., 511, 191-198 (2005).

Baiardo et al. "Thermal and Mechanical Properties of Plasticized Poly(L-lactic acid)" Journal of Applied Polymer Science, 90, 1731-1738 (2003).

Benny, O. "Local Delivery of Poly Lactic-co-glycolic Acid Microspheres Containing Imatinib Mesylate Inhibits Intracranial Xenograft Glioma Growth" Clin Cancer Res 2009; 15(4), 1222-1231.

(56) References Cited

OTHER PUBLICATIONS

Hedberg, et al. "Controlled release of an osteogenic peptide from injectable biodegradable polymeric composites" Journal of Controlled Release, 84, 137-150 (2002).
Hou, et al. "In Situ Gelling Hydogels Incorporating Microparticles as Drug Delivery Carriers for Regenerative Medicine" Journal of Pharmaceutical Sciences, 97, 3972-3980 (2008).
Jacobs et al. Polymer Delivery Systems Concepts in Polymeric Delivery Systems; El-Nokaly, M., et al.; ACS Symposium Series; American Chemical Society: Washington, DC, 1993.
Kirby, G. et al. "PLGA-Based Microparticles for the Sustained Release of BMP-2" Polymers 2011; 3(1), 571-586.
Rahman et al. "PLGA/PEG-hydrogel composite scaffolds with controllable mechanical properties" J. of Biomedical Materials Research, 101, 648-655, (2013).
Bungaard et al., "N-Sulfonyl Imidates as a Novel Prodrug Form for an Ester Function or a Sulfonamide Group," J. Med. Chem., 31:2066-2069 (1988).
Edwards et al., "Large porous particles for Pulmonary Drug Delivery," Science, 276:1868-1971 (1997).
Wagh et al., "Polymers used in ocular dosage form and drug delivery systems," Asian Journal of Pharmaceutics, 2(1):12-17 (2008).

\* cited by examiner

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Primer

<400> SEQUENCE: 1
attcctcagc catcatctgg                                        20

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
atttcgtggt ttgctgttcc                                        20

SUNITINIB FORMULATIONS AND METHODS FOR USE THEREOF IN TREATMENT OF GLAUCOMA

CROSS REFERENCE TO RELATED APPLICATIONS

This application is a 371 application of PCT/US2015/065878, filed Dec. 15, 2015, which claims priority to and benefit of U.S. Provisional Application No. 62/092,118 entitled "Controlled Release Sunitinib Formulations" filed on Dec. 15, 2014, and U.S. Provisional Application No. 62/139,306 "Method Of Prevention Of Corneal Neovascularization" filed Mar. 27, 2015, the disclosures of which are hereby incorporated herein by reference in their entirety.

REFERENCE TO SEQUENCE LISTING

The Sequence Listing submitted Dec. 15, 2015 as a text file named "JHU_C13492_PCT_ST25" created on Dec. 15, 2015, and having a size of 746 bytes is hereby incorporated by reference.

FIELD OF THE INVENTION

The present invention relates to sunitinib formulations and methods of use thereof, especially for use in the treatment of ocular diseases and other neuronal disorders.

BACKGROUND OF THE INVENTION

There are several types of glaucoma. The two main types are open-angle and angle-closure. These are marked by an increase of intraocular pressure (IOP), or pressure inside the eye.

Open-angle glaucoma, the most common form of glaucoma, accounting for at least 90% of all glaucoma cases, is caused by the slow clogging of the drainage canals, resulting in increased eye pressure. It has a wide and open angle between the iris and cornea, develops slowly and is a lifelong condition, and has symptoms and damage that are not noticed. "Open-angle" means that the angle where the iris meets the cornea is as wide and open as it should be. Open-angle glaucoma is also called primary or chronic glaucoma. It is the most common type of glaucoma, affecting about three million Americans.

Angle-closure glaucoma, a less common form of glaucoma: It is caused by blocked drainage canals, resulting in a sudden rise in intraocular pressure, has a closed or narrow angle between the iris and cornea, develops very quickly, has symptoms and damage that are usually very noticeable, and demands immediate medical attention. It is also called acute glaucoma or narrow-angle glaucoma. Unlike open-angle glaucoma, angle-closure glaucoma is a result of the angle between the iris and cornea closing.

Normal-Tension Glaucoma (NTG) or low-tension or normal-pressure glaucoma is where the optic nerve is damaged even though the eye pressure is not very high. Congenital Glaucoma occurs in babies when there is incorrect or incomplete development of the eye's drainage canals during the prenatal period. This is a rare condition that may be inherited. When uncomplicated, microsurgery can often correct the structural defects. Other cases are treated with medication and surgery. Other Types of Glaucoma include: Secondary Glaucoma, Pigmentary Glaucoma, Pseudoexfoliative Glaucoma, Traumatic Glaucoma, Neovascular Glaucoma, Irido Corneal Endothelial Syndrome (ICE), and Uveitic Glaucoma.

Open angle glaucoma is the most common form of glaucoma, affecting about three million Americans. It happens when the eye's drainage canals become clogged over time. The inner eye pressure (intraocular pressure or IOP) rises because the correct amount of fluid cannot drain out of the eye. With open-angle glaucoma, the entrances to the drainage canals are clear and should be working correctly. If open-angle glaucoma is not diagnosed and treated, it can cause a gradual loss of vision. This type of glaucoma develops slowly and sometimes without noticeable sight loss for many years. It usually responds well to medication, especially if caught early and treated.

Vision loss in glaucoma, a neurodegenerative disease that is the leading cause of irreversible blindness worldwide, is due to the dysfunction and death of retinal ganglion cells (RGCs). Current therapies all act by lowering intraocular pressure (IOP). However, pressure reduction can be difficult to achieve, and even with significant pressure lowering, RGC loss can continue. Efforts have therefore been made to develop neuroprotective agents that would complement IOP-lowering by directly inhibiting the RGC cell death process, though no neuroprotective agent is yet in clinical use.

It is an object of the invention to provide methods for encapsulation or incorporation into polymeric matrices, including nano- and micro-particles, with increased loading, of drugs for treatment of glaucoma and neuronal damage.

It is still another object of the invention to provide improved dosage formulations, prolonged pharmacokinetics, and methods of use thereof.

SUMMARY OF THE INVENTION

Methods for increasing the encapsulation or incorporation of Sunitinib into polymeric matrices have been developed. The resulting formulations provide for more sustained controlled release of sunitinib for reduction or prevention of neuronal death due to elevated intraocular pressure associated with glaucoma. Increased loading is achieved using an alkaline solvent system.

Examples demonstrate that polyesters such as PEG-PLGA (PLA) and PEG-PLGA/blend microparticles display sustained release of sunitinib. Polymer microparticles composed of PLGA and PEG covalently conjugated to PLGA ($M_w$ 45 kDa) (PLGA45k-PEG5k) loaded with Sunitinib were prepared using a single emulsion solvent evaporation method. Maximum loading was achieved by increasing the alkalinity of sunitinib, up to 16.1% with PEG-PLGA, which could be further increased by adding DMF, compared to only 1% with no alkaline added.

The drugs can be used to form implants (e.g., rods, discs, wafers, etc.), nanoparticles, or microparticles with improved properties for controlled delivery of drugs. Pharmaceutical compositions containing implants (e.g., rods, discs, wafers, etc.), nanoparticles, microparticles, or combinations thereof for the controlled release of the Sunitinib can be prepared by combining the drug in the matix with one or more pharmaceutically acceptable excipients. The nanoparticles, microparticles, or combination thereof can be formed from one or more drugs, or blends of drugs with one or more polymers.

It has been discovered that dual-leucine zipper kinase (DLK) is a key neuroprotective drug target of sunitinib. Supporting this finding, a number of other neuroprotective kinase inhibitors also inhibit DLK. Sustained controlled release formulations of these compounds can be administered to treat or reduce neuronal death due to elevated intraocular pressure. Examples demonstrate in animal models that the sunitinib formulations are efficacious in preventing optic nerve damage due to elevated intraocular pressure.

DETAILED DESCRIPTION OF THE INVENTION

I. Definitions

Figure 1A:
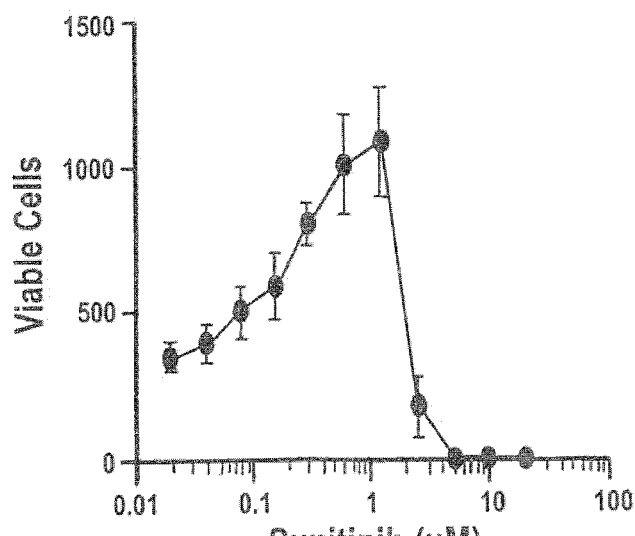
FIG. 1A is a graph showing sunitinib promotes RGC survival in vitro and in vivo, survival of immunopanned RGCs, treated with increasing doses of sunitinib, after 72 hours in culture.

"Active Agent," as used herein, refers to a physiologically or pharmacologically active substance that acts locally and/or systemically in the body. An active agent is a substance that is administered to a patient for the treatment (e.g., therapeutic agent), prevention (e.g., prophylactic agent), or diagnosis (e.g., diagnostic agent) of a disease or disorder. "Ophthalmic Drug" or "Ophthalmic Active Agent", as used herein, refers to an agent that is administered to a patient to alleviate, delay onset of, or prevent one or more symptoms of a disease or disorder of the eye, or diagnostic agent useful for imaging or otherwise assessing the eye.

"Effective amount" or "therapeutically effective amount," as used herein, refers to an amount of drug effective to alleviate, delay onset of, or prevent one or more symptoms, particularly of cancer or a disease or disorder of the eye. In the case of age-related macular degeneration, the effective amount of the drug delays, reduces, or prevents vision loss in a patient.

As used herein, the term "alkaline" refers to a compound capable of accepting an acidic proton or otherwise raising the pH of the composition.

"Biocompatible" and "biologically compatible," as used herein, generally refer to materials that are, along with any metabolites or degradation products thereof, generally non-toxic to the recipient, and do not cause any significant adverse effects to the recipient. Generally speaking, biocompatible materials are materials which do not elicit a significant inflammatory or immune response when administered to a patient.

"Biodegradable Polymer," as used herein, generally refers to a polymer that will degrade or erode by enzymatic action and/or hydrolysis under physiologic conditions to smaller units or chemical species that are capable of being metabolized, eliminated, or excreted by the subject. The degradation time is a function of polymer composition, morphology, such as porosity, particle dimensions, and environment.

"Hydrophilic," as used herein, refers to the property of having affinity for water. For example, hydrophilic polymers (or hydrophilic polymers) are polymers (or polymers) which are primarily soluble in aqueous solutions and/or have a tendency to absorb water. In general, the more hydrophilic a polymer is, the more that polymer tends to dissolve in, mix with, or be wetted by water.

"Hydrophobic," as used herein, refers to the property of lacking affinity for, or even repelling water. For example, the more hydrophobic a polymer (or polymer), the more that polymer (or polymer) tends to not dissolve in, not mix with, or not be wetted by water.

Hydrophilicity and hydrophobicity can be spoken of in relative terms, such as, but not limited to, a spectrum of hydrophilicity/hydrophobicity within a group of polymers or polymers. In some embodiments wherein two or more polymers are being discussed, the term "hydrophobic polymer" can be defined based on the polymer's relative hydrophobicity when compared to another, more hydrophilic polymer.

"Microparticle," as used herein, generally refers to a particle having a diameter, such as an average diameter, from about 1 micron to about 100 microns, preferably from about 1 micron to about 50 microns, more preferably from about 1 to about 30 microns. The microparticles can have any shape. Microparticles having a spherical shape are generally referred to as "microspheres".

"Molecular weight," as used herein, generally refers to the relative average chain length of the bulk polymer, unless otherwise specified. In practice, molecular weight can be estimated or characterized using various methods including gel permeation chromatography (GPC) or capillary viscometry. GPC molecular weights are reported as the weight-average molecular weight (Mw) as opposed to the number-average molecular weight (Mn). Capillary viscometry provides estimates of molecular weight as the inherent viscosity determined from a dilute polymer solution using a particular set of concentration, temperature, and solvent conditions.

"Mean particle size," as used herein, generally refers to the statistical mean particle size (diameter) of the particles in a population of particles. The diameter of an essentially spherical particle may refer to the physical or hydrodynamic diameter. The diameter of a non-spherical particle may refer preferentially to the hydrodynamic diameter. As used herein, the diameter of a non-spherical particle may refer to the largest linear distance between two points on the surface of the particle. Mean particle size can be measured using methods known in the art, such as dynamic light scattering.

"Monodisperse" and "homogeneous size distribution" are used interchangeably herein and describe a population of nanoparticles or microparticles where all of the particles are the same or nearly the same size. As used herein, a monodisperse distribution refers to particle distributions in which 90% or more of the distribution lies within 15% of the median particle size, more preferably within 10% of the median particle size, most preferably within 5% of the median particle size.

"Pharmaceutically Acceptable," as used herein, refers to compounds, carriers, excipients, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Implant," as generally used herein, refers to a polymeric device or element that is structured, sized, or otherwise configured to be implanted, preferably by injection or surgical implantation, in a specific region of the body so as to provide therapeutic benefit by releasing one or more active agents over an extended period of time at the site of implantation. For example, intraocular implants are polymeric devices or elements that are structured, sized, or otherwise configured to be placed in the eye, preferably by injection or surgical implantation, and to treat one or more diseases or disorders of the eye by releasing one or more drugs over an extended period. Intraocular implants are generally biocompatible with physiological conditions of an eye and do not cause adverse side effects. Generally, intraocular implants may be placed in an eye without disrupting vision of the eye.

II. Compositions

A. DLK Inhibitors

It has been discovered that dual-leucine zipper kinase (DLK) is a key neuroprotective drug target of sunitinib. Supporting this finding, a number of other neuroprotective kinase inhibitors also inhibit DLK. These include SR8165, axitinib, bosutinib, neratininb, crizotinib, tozasertib, lestautinib, foretinib, TAE-684 and KW-2449

Sustained controlled release formulations of these compounds can be administered to treat or reduce neuronal death due to elevated intraocular pressure.

It has been suggested that sunitinib may be useful for treatment of glaucoma. Sunitinib (marketed as SUTENT® by Pfizer, and previously known as SU11248) is an oral, small-molecule, multi-targeted receptor tyrosine kinase (RTK) inhibitor that was approved by the FDA for the treatment of renal cell carcinoma (RCC) and imatinib-resistant gastrointestinal stromal tumor (GIST) on Jan. 26, 2006. Sunitinib was the first cancer drug simultaneously approved for two different indications.

Sunitinib inhibits cellular signaling by targeting multiple receptor tyrosine kinases (RTKs). These include all receptors for platelet-derived growth factor (PDGF-Rs) and vascular endothelial growth factor receptors (VEGFRs), which play a role in both tumor angiogenesis and tumor cell proliferation. The simultaneous inhibition of these targets leads to both reduced tumor vascularization and cancer cell death, and, ultimately, tumor shrinkage. Sunitinib is also neuroprotective by virtue of its kinase inhibitory activity.

Sunitinib is a compound of formula (1):

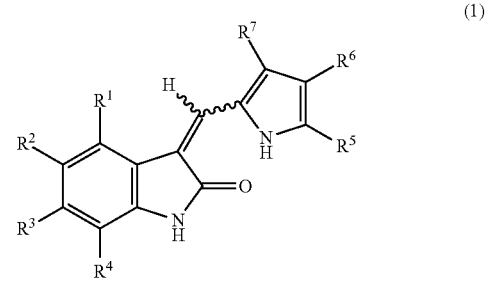

wherein $R^1$ is selected from the group consisting of hydrogen, halo, alkyl, cycloalkyl, aryl, heteroaryl, heteroalicyclic, hydroxy, alkoxy, —(CO)$R^{15}$, —NR$^{13}$R$^{14}$, —(CH$_2$)$_r$R$^{16}$ and —C(O)NR$^8$R$^9$;

$R^2$ is selected from the group consisting of hydrogen, halo, alkyl, trihalomethyl, hydroxy, alkoxy, cyano, —NR$^{13}$R$^{14}$, —NR$^{13}$C(O)R$^{14}$, —C(O)R$^{15}$, aryl, heteroaryl, —S(O)$_2$NR$^{13}$R$^{14}$ and —SO$_2$R$^{20}$ (wherein R$^{20}$ is alkyl, aryl, aralkyl, heteroaryl and heteroaralkyl);

$R^3$ is selected from the group consisting of hydrogen, halogen, alkyl, trihalomethyl, hydroxy, alkoxy, —(CO)R$^{15}$, —NR$^{13}$R$^{14}$, aryl, heteroaryl, —NR$^{13}$S(O)$_2$R$^{14}$, —S(O)$_2$NR$^{13}$R$^{14}$, —NR$^{13}$C(O)R$^{14}$, —NR$^{13}$C(O)OR$^{14}$ and —SO$_2$R$^{20}$ (wherein R$^{20}$ is alkyl, aryl, aralkyl, heteroaryl and heteroaralkyl);

$R^4$ is selected from the group consisting of hydrogen, halogen, alkyl, hydroxy, alkoxy and —NR$^{13}$R$^{14}$;

$R^5$ is selected from the group consisting of hydrogen, alkyl and —C(O)R$^{10}$;

$R^6$ is selected from the group consisting of hydrogen, alkyl and —C(O)R$^{10}$;

$R^7$ is selected from the group consisting of hydrogen, alkyl, aryl, heteroaryl, —C(O)R$^{17}$ and —C(O)R$^{10}$; or $R^6$ and $R^7$ may combine to form a group selected from the group consisting of —(CH$_2$)$_4$—, —(CH$_2$)$_5$— and —(CH$_2$)$_6$—; with the proviso that at least one of R$^5$, R$^6$ or R$^7$ must be —C(O)R$^{10}$;

$R^8$ and $R^9$ are independently selected from the group consisting of hydrogen, alkyl and aryl;

$R^{10}$ is selected from the group consisting of hydroxy, alkoxy, aryloxy, —N($R^{11}$) ($CH_2$)$_n R^{12}$, and —N$R^{13}R^{14}$;

$R^{11}$ is selected from the group consisting of hydrogen and alkyl;

$R^{12}$ is selected from the group consisting of —N$R^{13}R^{14}$, hydroxy, —C(O)$R^{15}$, aryl, heteroaryl, —N$^+$(O$^-$)$R^{13}R^{14}$, —N(OH)$R^{13}$, and —NHC(O)$R^a$ (wherein $R^a$ is unsubstituted alkyl, haloalkyl, or aralkyl);

$R^{13}$ and $R^{14}$ are independently selected from the group consisting of hydrogen, alkyl, cyanoalkyl, cycloalkyl, aryl and heteroaryl; or $R^{13}$ and $R^{14}$ may combine to form a heterocyclo group;

$R^{15}$ is selected from the group consisting of hydrogen, hydroxy, alkoxy and aryloxy;

$R^{16}$ is selected from the group consisting of hydroxy, —C(O)$R^{15}$, —N$R^{13}R^{14}$ and —C(O)N$R^{13}R^{14}$;

$R^{17}$ is selected from the group consisting of alkyl, cycloalkyl, aryl and heteroaryl;

$R^{20}$ is alkyl, aryl, aralkyl or heteroaryl; and n and r are independently 1, 2, 3, or 4;

or a pharmaceutically acceptable salt thereof.

In certain embodiments, the compound of formula 1 has the formula:

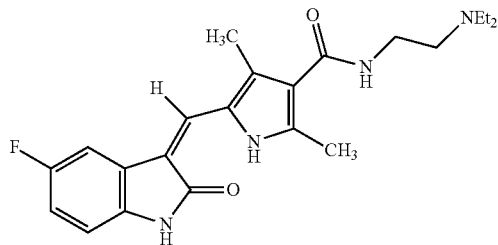

The following definitions are used herein:

"Alkyl" refers to a saturated aliphatic hydrocarbon radical including straight chain and branched chain groups of 1 to 20 carbon atoms (whenever a numerical range; e.g. "1-20", is stated herein, it means that the group, in this case the alkyl group, may contain 1 carbon atom, 2 carbon atoms, 3 carbon atoms, etc. up to and including 20 carbon atoms). Alkyl groups containing from 1 to 4 carbon atoms are referred to as lower alkyl groups. When the lower alkyl groups lack substituents, they are referred to as unsubstituted lower alkyl groups. More preferably, an alkyl group is a medium size alkyl having 1 to 10 carbon atoms e.g., methyl, ethyl, propyl, 2-propyl, n-butyl, iso-butyl, tert-butyl, and pentyl. Most preferably, it is a lower alkyl having 1 to 4 carbon atoms e.g., methyl, ethyl, propyl, 2-propyl, n-butyl, iso-butyl, or tert-butyl. The alkyl group may be substituted or unsubstituted. When substituted, the substituent group(s) is preferably one or more, more preferably one to three, even more preferably one or two substituent(s) independently selected from the group consisting of halo, hydroxy, unsubstituted lower alkoxy, aryl optionally substituted with one or more groups, preferably one, two or three groups which are independently of each other halo, hydroxy, unsubstituted lower alkyl or unsubstituted lower alkoxy groups, aryloxy optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 5- or 6-member heteroalicyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, mercapto, (unsubstituted lower alkyl)thio, arylthio optionally substituted with one or more groups, preferably one, two or three groups which are independently of each other halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}$S(O)—, $R^{18}$S(O)$_2$—, —C(O)O$R^{18}$, $R^{18}$C(O)O—, and —N$R^{18}R^{19}$, wherein $R^{18}$ and $R^{19}$ are independently selected from the group consisting of hydrogen, unsubstituted lower alkyl, trihalomethyl, unsubstituted ($C_3$-$C_6$)cycloalkyl, unsubstituted lower alkenyl, unsubstituted lower alkynyl and aryl optionally substituted with one or more, groups, preferably one, two or three groups which are independently of each other halo, hydroxy, unsubstituted lower alkyl or unsubstituted lower alkoxy groups.

Preferably, the alkyl group is substituted with one or two substituents independently selected from the group consisting of hydroxy, 5- or 6-member heteroalicyclic group having from 1 to 3 heteroatoms selected from the group consisting of nitrogen, oxygen and sulfur, the carbon and nitrogen (if present) atoms in the group being optionally substituted with one or more groups, preferably one, two or three groups which are independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and the nitrogen atoms in the group being optionally substituted with one or more groups, preferably one, two or three groups which are independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more groups, preferably one, two or three groups which are independently of each other halo, hydroxy, unsubstituted lower alkyl or unsubstituted lower alkoxy groups, or —N$R^{18}R^{19}$, wherein $R^{18}$ and $R^{19}$ are independently selected from the group consisting of hydrogen, unsubstituted lower alkyl. Even more preferably the alkyl group is substituted with one or two substituents which are independently of each other hydroxy, dimethylamino, ethylamino, diethylamino, dipropylamino, pyrrolidino, piperidino, morpholino, piperazino, 4-lower alkylpiperazino, phenyl, imidazolyl, pyridinyl, pyridazinyl, pyrimidinyl, oxazolyl, and triazinyl.

"Cycloalkyl" refers to a 3 to 8 member all-carbon monocyclic ring, an all-carbon 5-member/6-member or 6-member/6-member fused bicyclic ring or a multicyclic fused ring (a "fused" ring system means that each ring in the system shares an adjacent pair of carbon atoms with each other ring in the system) group wherein one or more of the rings may contain one or more double bonds but none of the rings has a completely conjugated pi-electron system. Examples of cycloalkyl groups are cyclopropane, cyclobutane, cyclopentane, cyclopentene, cyclohexane, cyclohexadiene, adamantane, cycloheptane, and cycloheptatriene. A cycloalkyl group may be substituted or unsubstituted. When substituted, the substituent group(s) is preferably one or more, more preferably one or two substituents, independently selected from the group consisting of unsubstituted lower alkyl, trihaloalkyl, halo, hydroxy, unsubstituted lower alkoxy, aryl optionally substituted with one or more, preferably one or two groups independently of each other halo, hydroxy, unsubstituted lower alkyl or unsubstituted lower alkoxy groups, aryloxy optionally substituted with one or more, preferably one or two groups independently of each other halo, hydroxy, unsubstituted lower alkyl or unsubstituted lower alkoxy groups, 6-member heteroaryl having from 1 to 3 nitrogen atoms in the ring, the carbons in the ring being optionally substituted with one or more, preferably one or two groups independently of each other halo, hydroxy, unsubstituted lower alkyl or unsubstituted lower alkoxy groups, 5-member heteroaryl having from 1 to 3 heteroatoms selected from the group consisting of nitrogen, oxygen and sulfur, the carbon and nitrogen atoms of the group being optionally substituted with one or more, preferably one or two groups independently of each other halo, hydroxy, unsubstituted lower alkyl or unsubstituted lower alkoxy groups, 5- or 6-member heteroalicyclic group having from 1 to 3 heteroatoms selected from the group consisting of nitrogen, oxygen and sulfur, the carbon and nitrogen (if present) atoms in the group being optionally substituted with one or more, preferably one or two groups independently of each other halo, hydroxy, unsubstituted lower alkyl or unsubstituted lower alkoxy groups, mercapto, (unsubstituted lower alkyl)thio, arylthio optionally substituted with one or more, preferably one or two groups independently of each other halo, hydroxy, unsubstituted lower alkyl or unsubstituted lower alkoxy groups, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}S(O)_2$—, —$C(O)OR^{18}$, $R^{18}C(O)O$—, and —$NR^{18}R^{19}$ are as defined above.

"Alkenyl" refers to a lower alkyl group, as defined herein, consisting of at least two carbon atoms and at least one carbon-carbon double bond. Representative examples include, but are not limited to, ethenyl, 1-propenyl, 2-propenyl, and 1-, 2-, or 3-butenyl.

"Alkynyl" refers to a lower alkyl group, as defined herein, consisting of at least two carbon atoms and at least one carbon-carbon triple bond. Representative examples include, but are not limited to, ethynyl, 1-propynyl, 2-propynyl, and 1-, 2-, or 3-butynyl.

"Aryl" refers to an all-carbon monocyclic or fused-ring polycyclic (i.e., rings which share adjacent pairs of carbon atoms) groups of 1 to 12 carbon atoms having a completely conjugated pi-electron system. Examples, without limitation, of aryl groups are phenyl, naphthalenyl and anthracenyl. The aryl group may be substituted or unsubstituted. When substituted, the substituted group(s) is preferably one or more, more preferably one, two or three, even more preferably one or two, independently selected from the group consisting of unsubstituted lower alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}S(O)_2$—, —$C(O)OR^{18}$, $R^{18}C(O)O$—, and —$NR^{18}R^{19}$, with $R^{18}$ and $R^{19}$ as defined above. Preferably, the aryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

"Heteroaryl" refers to a monocyclic or fused ring (i.e., rings which share an adjacent pair of atoms) group of 5 to 12 ring atoms containing one, two, or three ring heteroatoms selected from N, O, or S, the remaining ring atoms being C, and, in addition, having a completely conjugated pi-electron system. Examples, without limitation, of unsubstituted heteroaryl groups are pyrrole, furan, thiophene, imidazole, oxazole, thiazole, pyrazole, pyridine, pyrimidine, quinoline, isoquinoline, purine and carbazole. The heteroaryl group may be substituted or unsubstituted. When substituted, the substituted group(s) is preferably one or more, more preferably one, two, or three, even more preferably one or two, independently selected from the group consisting of unsubstituted lower alkyl, trihaloalkyl, halo, hydroxy, unsubstituted lower alkoxy, mercapto, (unsubstituted lower alkyl) thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}O)_2$—, —$C(O)OR^{18}$, $R^{18}C(O)O$—, and —$NR^{18}R^{19}$, with $R^{18}$ and $R^{19}$ as defined above. Preferably, the heteroaryl group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

"Heteroalicyclic" refers to a monocyclic or fused ring group having in the ring(s) of 5 to 9 ring atoms in which one or two ring atoms are heteroatoms selected from N, O, or $S(O)_n$ (where n is an integer from 0 to 2), the remaining ring atoms being C. The rings may also have one or more double bonds. However, the rings do not have a completely conjugated pi-electron system. Examples, without limitation, of unsubstituted heteroalicyclic groups are pyrrolidino, piperidino, piperazino, morpholino, thiomorpholino, and homopiperazino. The heteroalicyclic ring may be substituted or unsubstituted. When substituted, the substituted group(s) is preferably one or more, more preferably one, two or three, even more preferably one or two, independently selected from the group consisting of unsubstituted lower-alkyl, trihaloalkyl, halo, hydroxy, unsubstituted lower alkoxy, mercapto, (unsubstituted lower alkyl)thio, cyano, acyl, thioacyl, O-carbamyl, N-carbamyl, O-thiocarbamyl, N-thiocarbamyl, C-amido, N-amido, nitro, N-sulfonamido, S-sulfonamido, $R^{18}S(O)$—, $R^{18}S(O)_2$—, —$C(O)OR^{18}$, $R^{18}C(O)O$—, and —$NR^{18}R^{19}$, with $R^{18}$ and $R^{19}$ as defined above. Preferably, the heteroalicyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

Preferably, the heteroalicyclic group is optionally substituted with one or two substituents independently selected from halo, unsubstituted lower alkyl, trihaloalkyl, hydroxy, mercapto, cyano, N-amido, mono or dialkylamino, carboxy, or N-sulfonamido.

"Heterocycle" means a saturated cyclic radical of 3 to 8 ring atoms in which one or two ring atoms are heteroatoms selected from N, O, or $S(O)_n$ (where n is an integer from 0 to 2), the remaining ring atoms being C, where one or two C atoms may optionally be replaced by a carbonyl group. The heterocyclyl ring may be optionally substituted independently with one, two, or three substituents selected from optionally substituted lower alkyl (substituted with 1 or 2 substituents independently selected from carboxy or ester), haloalkyl, cyanoalkyl, halo, nitro, cyano, hydroxy, alkoxy, amino, monoalkylamino, dialkylamino, aralkyl, heteroaralkyl, —COR (where R is alkyl) or —COOR where R is (hydrogen or alkyl). More specifically the term heterocyclyl includes, but is not limited to, tetrahydropyranyl, 2,2-dimethyl-1,3-dioxolane, piperidino, N-methylpiperidin-3-yl, piperazino, N-methylpyrrolidin 3-yl, 3-pyrrolidino, morpholino, thiomorpholino, thiomorpholino-1-oxide, thiomorpholino 1,1-dioxide, 4-ethyloxycarbonylpiperazino, 3-oxopiperazino, 2-imidazolidone, 2-pyrrolidinone, 2-oxohomopiperazino, tetrahydropyrimidin-2-one, and the derivatives thereof. Preferably, the heterocycle group is optionally substituted with one or two substituents independently selected from halo, unsubstituted lower alkyl, lower alkyl substituted with carboxy, ester, hydroxy, mono or dialkylamino.

"Hydroxy" refers to an —OH group.

"Alkoxy" refers to both an —O-(unsubstituted alkyl) and an —O-(unsubstituted cycloalkyl) group. Representative examples include, but are not limited to, e.g., methoxy, ethoxy, propoxy, butoxy, cyclopropyloxy, cyclobutyloxy, cyclopentyloxy, and cyclohexyloxy.

"Aryloxy" refers to both an —O-aryl and an —O-heteroaryl group, as defined herein. Representative examples include, but are not limited to, phenoxy, pyridinyloxy, furanyloxy, thienyloxy, pyrimidinyloxy, pyrazinyloxy, and derivatives thereof.

"Mercapto" refers to an —SH group.

"Alkylthio" refers to both an —S-(unsubstituted alkyl) and an —S-(unsubstituted cycloalkyl) group. Representative examples include, but are not limited to, e.g., methylthio, ethylthio, propylthio, butylthio, cyclopropylthio, cyclobutylthio, cyclopentylthio, and cyclohexylthio.

"Arylthio" refers to both an —S-aryl and an —S-heteroaryl group, as defined herein. Representative examples include, but are not limited to, phenylthio, pyridinylthio, furanylthio, thientylthio, pyrimidinylthio, and derivatives thereof.

"Acyl" refers to a —C(O)—R" group, where R" is selected from the group consisting of hydrogen, unsubstituted lower alkyl, trihalomethyl, unsubstituted cycloalkyl, aryl optionally substituted with one or more, preferably one, two, or three substituents selected from the group consisting of unsubstituted lower alkyl, trihalomethyl, unsubstituted lower alkoxy, halo and —NR$^{18}$R$^{19}$ groups, heteroaryl (bonded through a ring carbon) optionally substituted with one or more, preferably one, two, or three substitutents selected from the group consisting of unsubstituted lower alkyl, trihaloalkyl, unsubstituted lower alkoxy, halo and —NR$^{18}$R$^{19}$ groups and heteroalicyclic (bonded through a ring carbon) optionally substituted with one or more, preferably one, two, or three substituents selected from the group consisting of unsubstituted lower alkyl, trihaloalkyl, unsubstituted lower alkoxy, halo and —NR$^{18}$R$^{19}$ groups. Representative acy groups include, but are not limited to, acetyl, trifluoroacetyl, and benzoyl.

"Aldehyde" refers to an acyl group in which R" is hydrogen.

"Thioacyl" refers to a —C(S)—R" group, with R" as defined herein.

"Ester" refers to a —C(O)O—R" group with R" as defined herein except that R" cannot be hydrogen.

"Acetyl" group refers to a —C(O)CH$_3$ group.

"Halo" group refers to fluorine, chlorine, bromine or iodine, preferably fluorine or chlorine.

"Trihalomethyl" group refers to a —CX$_3$ group wherein X is a halo group as defined herein.

"Trihalomethanesulfonyl" group refers to a X$_3$CS(=O)$_2$— groups with X as defined above.

"Cyano" refers to a —C≡N group.

"Methylenedioxy" refers to a —OCH$_2$O— group where the two oxygen atoms are bonded to adjacent carbon atoms.

"Ethylenedioxy" group refers to a —OCH$_2$CH$_2$O— where the two oxygen atoms are bonded to adjacent carbon atoms.

"S-sulfonamido" refers to a —S(O)$_2$NR$^{18}$R$^{19}$ group, with R$^{18}$ and R$^{19}$ as defined herein. "N-sulfonamido" refers to a —NR$^{18}$S(O)$_2$R$^{19}$— group, with R$^{18}$ and R$^{19}$ as defined herein.

"O-carbamyl" group refers to a —OC(O)NR$^{18}$R$^{19}$ group with R$^{18}$ and R$^{19}$ as defined herein. "N-carbamyl" refers to an R$^{18}$O C(O)NR$^{19}$— group, with R$^{18}$ and R$^{19}$ as defined herein.

"O-thiocarbamyl" refers to a —OC(S)NR$^{18}$R$^{19}$ group with R$^{18}$ and R$^{19}$ as defined herein. "N-thiocarbamyl" refers to a R$^{18}$OC(S)NR$^{19}$— group, with R$^{18}$ and R$^{19}$ as defined herein.

"Amino" refers to an —NR$^{18}$R$^{19}$ group, wherein R$^{18}$ and R$^{19}$ are both hydrogen.

"C-amido" refers to a —C(O)NR$^{18}$R$^{19}$ group with R$^{18}$ and R$^{19}$ as defined herein. "N-amido" refers to a R$^{18}$C(O)NR$^{19}$— group, with R$^{18}$ and R$^{19}$ as defined herein.

"Nitro" refers to a NO$_2$ group.

"Haloalkyl" means an unsubstituted alkyl, preferably unsubstituted lower alkyl as defined above that is substituted with one or more same or different halo atoms, e.g., —CH$_2$Cl, —CF$_3$, —CH$_2$CF$_3$, and —CH$_2$CCl$_3$.

"Aralkyl" means unsubstituted alkyl, preferably unsubstituted lower alkyl as defined above which is substituted with an aryl group as defined above, e.g., —CH$_2$phenyl, —(CH$_2$)$_2$phenyl, —(CH$_2$)$_3$phenyl, CH$_3$CH(CH$_3$) CH$_2$phenyl, and derivatives thereof.

"Heteroaralkyl" group means unsubstituted alkyl, preferably unsubstituted lower alkyl as defined above, e.g., —CH$_2$phenyl, —(CH$_2$)$_2$phenyl, —(CH$_2$)$_3$phenyl, CH$_3$CH (CH$_3$)CH$_2$phenyl, and derivatives thereof.

"Dialkylamino" means a radical —NRR where each R is independently an unsubstituted alkyl or unsubstituted cycloalkyl group as defined above, e.g., dimethylamino, diethylamino, (1-methylethyl)-ethylamino, cyclohexylmethylamino, and cyclopentylmethylamino.

"Cyanoalkyl" means unsubstituted alkyl, preferably unsubstituted lower alkyl as defined above, which is substituted with 1 or 2 cyano groups.

"Optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocyclo group is not substituted with the alkyl group.

B. Encapsulating Polymers

Controlled release dosage formulations for the delivery of one or more drugs in a polymeric vehicle are described herein. The polymeric matrix can be formed from non-biodegradable or biodegradable polymers; however, the polymer matrix is preferably biodegradable. The polymeric matrix can be formed into implants (e.g., rods, disks, wafers, etc.), microparticles, nanoparticles, or combinations thereof for delivery. Upon administration, the sunitinib is released over an extended period of time, either upon degradation of the polymer matrix, diffusion of the one or more inhibitors out of the polymer matrix, or a combination thereof. The drug can be dispersed or encapsulated into the polymer or covalently bound to the polymer used to form the matrix. The degradation profile of the one or more polymers may be selected to influence the release rate of the active agent in vivo.

The polymers may be hydrophobic, hydrophilic, conjugates of hydrophilic and hydrophobic polymers (i.e., amphiphilic polymers), block co-polymers, and blends thereof.

Examples of suitable hydrophobic polymers include, but are not limited to, polyhydroxyesters such as polylactic acid, polyglycolic acid, or copolymers thereof, polycaprolactone, polyanhydrides such as polysebacic anhydride, and copolymers of any of the above.

The one or more hydrophilic polymers can be any hydrophilic, biocompatible, non-toxic polymer or copolymer. In certain embodiments, the one or more hydrophilic polymers contain a poly(alkylene glycol), such as polyethylene glycol (PEG). In particular embodiments, the one or more hydrophilic polymers are linear PEG chains.

Representative synthetic polymers include poly(hydroxy acids) such as poly(lactic acid), poly(glycolic acid), and poly(lactic acid-co-glycolic acid), poly(lactide), poly(glycolide), poly(lactide-co-glycolide), polyanhydrides, polyorthoesters, polyamides, polycarbonates, polyalkylenes such as polyethylene and polypropylene, polyalkylene glycols such as poly(ethylene glycol), polyalkylene oxides such as poly(ethylene oxide), polyalkylene terephthalates such as poly(ethylene terephthalate), polyvinyl alcohols, polyvinyl ethers, polyvinyl esters, polyvinyl halides such as poly(vinyl chloride), polyvinylpyrrolidone, polysiloxanes, poly(vinyl alcohols), poly(vinyl acetate), polystyrene, polyurethanes and co-polymers thereof, celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "celluloses"), polymers of acrylic acid, methacrylic acid or copolymers or derivatives thereof including esters, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) (jointly referred to herein as "polyacrylic acids"), poly(butyric acid), poly(valeric acid), and poly(lactide-co-caprolactone), copolymers and blends thereof. As used herein, "derivatives" include polymers having substitutions, additions of chemical groups, for example, alkyl, alkylene, hydroxylations, oxidations, and other modifications routinely made by those skilled in the art.

Examples of preferred natural polymers include proteins such as albumin and prolamines, for example, zein, and polysaccharides such as alginate, cellulose and polyhydroxyalkanoates, for example, polyhydroxybutyrate.

Examples of preferred non-biodegradable polymers include ethylene vinyl acetate, poly(meth)acrylic acid, polyamides, copolymers and mixtures thereof.

C. Alkalizing Agents

It was discovered that the loading of sunitinib can be increased by increasing the alkalinity of the sunitinib in solution during encapsulation. This can be achieved by selection of the solvent, adding alkalizing agents to the solvent, or including alkaline drugs with the sunitini. Examples of compounds that can be added for this purpose include solvents or solvent additives such as DMA, DMTA, TEA, aniline, ammonium, and sodium hydroxide, drugs such as Vitamin B4, caffeine, alkaloids, nicotine, the analgesic morphine, the antibacterial berberine, the anticancer compound vincristine, the antihypertension agent reserpine, the cholinomimetic galantamine, the anticholinergic agent atropine, the vasodilator vincamine, the antiarrhythmia compound quinidine, the antiasthma therapeutic ephedrine, and the antimalarial drug quinine.

III. Methods of Forming Microparticles, Nanoparticles and Implants

A. Micro and Nanoparticle Formation

Microparticle and nanoparticles can be formed using any suitable method for the formation of polymer micro- or nanoparticles known in the art. The method employed for particle formation will depend on a variety of factors, including the characteristics of the polymers present in the drug or polymer matrix, as well as the desired particle size and size distribution. The type of drug(s) being incorporated in the particles may also be a factor as some Drugs are unstable in the presence of certain solvents, in certain temperature ranges, and/or in certain pH ranges.

Particles having an average particle size of between 10 nm and 1000 microns are useful in the compositions described herein. In preferred embodiments, the particles have an average particle size of between 10 nm and 100 microns, more preferably between about 100 nm and about 50 microns, more preferably between about 200 nm and about 50 microns. The particles can have any shape but are generally spherical in shape.

Preferably, particles formed from one or more drugs contain significant amounts of a hydrophilic polymer, such as PEG, on their surface. In circumstances where a monodisperse population of particles is desired, the particles may be formed using a method which produces a monodisperse population of nanoparticles. Alternatively, methods producing polydisperse nanoparticle distributions can be used, and the particles can be separated using methods known in the art, such as sieving, following particle formation to provide a population of particles having the desired average particle size and particle size distribution.

Common techniques for preparing microparticles and nanoparticles include, but are not limited to, solvent evaporation, hot melt particle formation, solvent removal, spray drying, phase-inversion, coacervation, and low temperature casting. Suitable methods of particle formulation are briefly described below. Pharmaceutically acceptable excipients, including pH modifying agents, disintegrants, preservatives, and antioxidants, can optionally be incorporated into the particles during particle formation.

1. Solvent Evaporation

In this method, the drug (or polymer matrix and one or more Drugs) is dissolved in a volatile organic solvent, such as methylene chloride. The organic solution containing the drug is then suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

Drugs which contain labile polymers, such as certain polyanhydrides, may degrade during the fabrication process due to the presence of water. For these polymers, the following two methods, which are performed in completely anhydrous organic solvents, can be used.

2. Solvent Removal

Solvent removal can also be used to prepare particles from drugs that are hydrolytically unstable. In this method, the drug (or polymer matrix and one or more Drugs) is dispersed or dissolved in a volatile organic solvent such as methylene chloride. This mixture is then suspended by stirring in an organic oil (such as silicon oil) to form an emulsion. Solid particles form from the emulsion, which can subsequently be isolated from the supernatant. The external morphology of spheres produced with this technique is highly dependent on the identity of the drug.

3. Spray Drying

In this method, the drug (or polymer matrix and one or more Drugs) is dissolved in an organic solvent such as methylene chloride. The solution is pumped through a micronizing nozzle driven by a flow of compressed gas, and the resulting aerosol is suspended in a heated cyclone of air, allowing the solvent to evaporate from the microdroplets, forming particles. Particles ranging between 0.1-10 microns can be obtained using this method.

4. Phase Inversion

Particles can be formed from drugs using a phase inversion method. In this method, the drug (or polymer matrix and one or more Drugs) is dissolved in a "good" solvent, and the solution is poured into a strong non solvent for the drug to spontaneously produce, under favorable conditions, microparticles or nanoparticles. The method can be used to produce nanoparticles in a wide range of sizes, including, for example, about 100 nanometers to about 10 microns, typically possessing a narrow particle size distribution.

5. Coacervation

Techniques for particle formation using coacervation are known in the art, for example, in GB-B-929 406; GB-B-929 40 1; and U.S. Pat. Nos. 3,266,987, 4,794,000, and 4,460, 563. Coacervation involves the separation of a drug (or polymer matrix and one or more Drugs) solution into two immiscible liquid phases. One phase is a dense coacervate phase, which contains a high concentration of the drug, while the second phase contains a low concentration of the drug. Within the dense coacervate phase, the drug forms nanoscale or microscale droplets, which harden into particles. Coacervation may be induced by a temperature change, addition of a non-solvent or addition of a micro-salt (simple coacervation), or by the addition of another polymer thereby forming an interpolymer complex (complex coacervation).

6. Low Temperature Casting

Methods for very low temperature casting of controlled release microspheres are described in U.S. Pat. No. 5,019, 400 to Gombotz et al. In this method, the drug (or polymer matrix and sunitinib) is dissolved in a solvent. The mixture is then atomized into a vessel containing a liquid non-solvent at a temperature below the freezing point of the drug solution which freezes the drug droplets. As the droplets and non-solvent for the drug are warmed, the solvent in the droplets thaws and is extracted into the non-solvent, hardening the microspheres.

D. Implants

Implants can be formed which encapsulate and/or have dispersed therein the drug. In preferred embodiments, the implants are intraocular implants. Suitable implants include, but are not limited to, rods, discs, and wafers. The matrix can be formed of any of the non-biodegradable or biodegradable polymers described above, although biodegradable polymers are preferred. The composition of the polymer matrix is selected based on the time required for in vivo stability, i.e. that time required for distribution to the site where delivery is desired, and the time desired for delivery.

The implants may be of any geometry such as fibers, sheets, films, microspheres, spheres, circular discs, rods, or plaques. Implant size is determined by factors such as toleration for the implant, location of the implant, size limitations in view of the proposed method of implant insertion, ease of handling, etc.

Where sheets or films are employed, the sheets or films will be in the range of at least about 0.5 mm×0.5 mm, usually about 3 to 10 mm×5 to 10 mm with a thickness of about 0.1 to 1.0 mm for ease of handling Where fibers are employed, the fiber diameter will generally be in the range of about 0.05 to 3 mm and the fiber length will generally be in the range of about 0.5 to 10 mm.

The size and shape of the implant can also be used to control the rate of release, period of treatment, and drug concentration at the site of implantation. Larger implants will deliver a proportionately larger dose, but depending on the surface to mass ratio, may have a slower release rate. The particular size and geometry of the implant are chosen to suit the site of implantation.

Intraocular implants may be spherical or non-spherical in shape. For spherical-shaped implants, the implant may have a largest dimension (e.g., diameter) between about 5 µm and about 2 mm, or between about 10 µm and about 1 mm for administration with a needle, greater than 1 mm, or greater than 2 mm, such as 3 mm or up to 10 mm, for administration by surgical implantation. If the implant is non-spherical, the implant may have the largest dimension or smallest dimension be from about 5 µm and about 2 mm, or between about 10 µm and about 1 mm for administration with a needle, greater than 1 mm, or greater than 2 mm, such as 3 mm or up to 10 mm, for administration by surgical implantation.

The vitreous chamber in humans is able to accommodate relatively large implants of varying geometries, having lengths of, for example, 1 to 10 mm. The implant may be a cylindrical pellet (e.g., rod) with dimensions of about 2 mm×0.75 mm diameter. The implant may be a cylindrical pellet with a length of about 7 mm to about 10 mm, and a diameter of about 0.75 mm to about 1.5 mm. In certain embodiments, the implant is in the form of an extruded filament with a diameter of about 0.5 mm, a length of about 6 mm, and a weight of approximately 1 mg. In some embodiments, the dimension are, or are similar to, implants already approved for intraocular injection via needle: diameter of 460 microns and a length of 6 mm and diameter of 370 microns and length of 3.5 mm.

Intraocular implants may also be designed to be least somewhat flexible so as to facilitate both insertion of the implant in the eye, such as in the vitreous, and subsequent accommodation of the implant. The total weight of the implant is usually about 250 to 5000 µg, more preferably about 500-1000 µg. In certain embodiments, the intraocular implant has a mass of about 500 µg, 750 µg, or 1000 µg.

2. Methods of Manufacture

Implants can be manufactured using any suitable technique known in the art. Examples of suitable techniques for the preparation of implants include solvent evaporation methods, phase separation methods, interfacial methods, molding methods, injection molding methods, extrusion methods, coextrusion methods, carver press method, die cutting methods, heat compression, and combinations thereof. Suitable methods for the manufacture of implants can be selected in view of many factors including the properties of the polymer/polymers present in the implant, the properties of the one or more drugs present in the implant, and the desired shape and size of the implant. Suitable methods for the preparation of implants are described, for example, in U.S. Pat. No. 4,997,652 and U.S. Patent Application Publication No. US 2010/0124565.

In certain cases, extrusion methods may be used to avoid the need for solvents during implant manufacture. When using extrusion methods, the polymer/polymers and Drug are chosen so as to be stable at the temperatures required for manufacturing, usually at least about 85° C. However, depending on the nature of the polymeric components and the one or more Drugs, extrusion methods can employ temperatures of about 25° C. to about 150° C., more preferably about 65° C. to about 130° C. Implants may be coextruded in order to provide a coating covering all or part of the surface of the implant. Such coatings may be erodible or non-erodible, and may be impermeable, semi-permeable, or permeable to the Drug, water, or combinations thereof. Such coatings can be used to further control release of the Drug from the implant.

Compression methods may be used to make the implants.

Compression methods frequently yield implants with faster release rates than extrusion methods. Compression methods may employ pressures of about 50-150 psi, more preferably about 70-80 psi, even more preferably about 76 psi, and use temperatures of about 0° C. to about 115° C., more preferably about 25° C.

IV. Pharmaceutical Formulations

A. Pharmaceutical Excipients

Pharmaceutical formulations contain sunitinib in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials which are generally recognized as safe (GRAS), and may be administered to an individual without causing undesirable biological side effects or unwanted interactions.

In some cases, the pharmaceutical formulation contains only one type of conjugate or polymeric particles for the controlled release of Drugs (e.g., a formulation containing drug particles wherein the drug particles incorporated into the pharmaceutical formulation have the same composition). In other embodiments, the pharmaceutical formulation contains two or more different type of conjugates or polymeric particles for the controlled release of Drugs (e.g., the pharmaceutical formulation contains two or more populations of drug particles, wherein the populations of drug particles have different chemical compositions, different average particle sizes, and/or different particle size distributions).

Particles formed from the drugs will preferably be formulated as a solution or suspension for injection to the eye or into a tissue such as a tumor.

Pharmaceutical formulations for ocular administration are preferably in the form of a sterile aqueous solution or suspension of particles formed from sunitinib. Acceptable solvents include, for example, water, Ringer's solution, phosphate buffered saline (PBS), and isotonic sodium chloride solution. The formulation may also be a sterile solution, suspension, or emulsion in a nontoxic, parenterally acceptable diluent or solvent such as 1,3-butanediol.

In some instances, the formulation is distributed or packaged in a liquid form. Alternatively, formulations for ocular administration can be packed as a solid, obtained, for example by lyophilization of a suitable liquid formulation. The solid can be reconstituted with an appropriate carrier or diluent prior to administration.

Solutions, suspensions, or emulsions for ocular administration may be buffered with an effective amount of buffer necessary to maintain a pH suitable for ocular administration. Suitable buffers are well known by those skilled in the art and some examples of useful buffers are acetate, borate, carbonate, citrate, and phosphate buffers.

Solutions, suspensions, or emulsions for ocular administration may also contain one or more tonicity agents to adjust the isotonic range of the formulation. Suitable tonicity agents are well known in the art and some examples include glycerin, mannitol, sorbitol, sodium chloride, and other electrolytes.

Solutions, suspensions, or emulsions for ocular administration may also contain one or more preservatives to prevent bacterial contamination of the ophthalmic preparations. Suitable preservatives are known in the art, and include polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions for ocular administration may also contain one or more excipients known art, such as dispersing agents, wetting agents, and suspending agents.

B. Additional Active Agents

In addition to the sunitinib present in the polymeric particles, the formulation can contain one or more additional therapeutic, diagnostic, and/or prophylactic agents. The active agents can be a small molecule active agent or a biomolecule, such as an enzyme or protein, polypeptide, or nucleic acid. Suitable small molecule active agents include organic and organometallic compounds. In some instances, the small molecule active agent has a molecular weight of less than about 2000 g/mol, more preferably less than about 1500 g/mol, most preferably less than about 1200 g/mol. The small molecule active agent can be a hydrophilic, hydrophobic, or amphiphilic compound.

In some cases, one or more additional active agents may be encapsulated in, dispersed in, or otherwise associated with the particles. In certain embodiments, one or more additional active agents may also be dissolved or suspended in the pharmaceutically acceptable carrier.

In the case of pharmaceutical compositions for the treatment of ocular diseases, the formulation may contain one or more ophthalmic drugs. In particular embodiments, the ophthalmic drug is a drug used to treat, prevent or diagnose a disease or disorder of the posterior segment eye. Non-limiting examples of ophthalmic drugs include anti-glaucoma agents, anti-angiogenesis agents, anti-infective agents, anti-inflammatory agents, growth factors, immunosuppressant agents, anti-allergic agents, and combinations thereof.

Representative anti-glaucoma agents include prostaglandin analogs (such as travoprost, bimatoprost, and latanoprost), beta-andrenergic receptor antagonists (such as timolol, betaxolol, levobetaxolol, and carteolol), alpha-2 adrenergic receptor agonists (such as brimonidine and apraclonidine), carbonic anhydrase inhibitors (such as brinzolamide, acetazolamine, and dorzolamide), miotics (i.e., parasympathomimetics, such as pilocarpine and ecothiopate), seretonergics muscarinics, dopaminergic agonists, and adrenergic agonists (such as apraclonidine and brimonidine).

Representative anti-angiogenesis agents include, but are not limited to, antibodies to vascular endothelial growth factor (VEGF) such as bevacizumab (AVASTIN®) and rhuFAb V2 (ranibizumab, LUCENTIS®), and other anti-VEGF compounds including aflibercept (EYLEA®); MACUGEN® (pegaptanim sodium, anti-VEGF aptamer or EYE001) (Eyetech Pharmaceuticals); pigment epithelium derived factor(s) (PEDF); COX-2 inhibitors such as celecoxib (CELEBREX®) and rofecoxib (VIOXX®); interferon alpha; interleukin-12 (IL-12); thalidomide (THALOMID®) and derivatives thereof such as lenalidomide (REVLIMID®); squalamine; endostatin; angiostatin; ribozyme inhibitors such as ANGIOZYME® (Sirna Therapeutics); multifunctional antiangiogenic agents such as NEOVASTAT® (AE-941) (Aeterna Laboratories, Quebec City, Canada); receptor tyrosine kinase (RTK) inhibitors such as sunitinib (SUTENT®); tyrosine kinase inhibitors such as sorafenib (Nexavar®) and erlotinib (Tarceva®); antibodies to the epidermal grown factor receptor such as panitumumab (VECTIBIX®) and cetuximab (ERBITUX®), as well as other anti-angiogenesis agents known in the art.

Anti-infective agents include antiviral agents, antibacterial agents, antiparasitic agents, and anti-fungal agents. Representative antiviral agents include ganciclovir and acyclovir. Representative antibiotic agents include aminoglycosides such as streptomycin, amikacin, gentamicin, and tobramycin, ansamycins such as geldanamycin and herbimycin, carbacephems, carbapenems, cephalosporins, glycopeptides such as vancomycin, teicoplanin, and telavancin, lincosamides, lipopeptides such as daptomycin, macrolides such as azithromycin, clarithromycin, dirithromycin, and erythromycin, monobactams, nitrofurans, penicillins, polypeptides such as bacitracin, colistin and polymyxin B, quinolones, sulfonamides, and tetracyclines.

In some cases, the active agent is an anti-allergic agent such as olopatadine and epinastine.

Anti-inflammatory agents include both non-steroidal and steroidal anti-inflammatory agents. Suitable steroidal active agents include glucocorticoids, progestins, mineralocorticoids, and corticosteroids.

The ophthalmic drug may be present in its neutral form, or in the form of a pharmaceutically acceptable salt. In some cases, it may be desirable to prepare a formulation containing a salt of an active agent due to one or more of the salt's advantageous physical properties, such as enhanced stability or a desirable solubility or dissolution profile.

Generally, pharmaceutically acceptable salts can be prepared by reaction of the free acid or base forms of an active agent with a stoichiometric amount of the appropriate base or acid in water or in an organic solvent, or in a mixture of the two; generally, non-aqueous media like ether, ethyl acetate, ethanol, isopropanol, or acetonitrile are preferred. Pharmaceutically acceptable salts include salts of an active agent derived from inorganic acids, organic acids, alkali metal salts, and alkaline earth metal salts as well as salts formed by reaction of the drug with a suitable organic ligand (e.g., quaternary ammonium salts). Lists of suitable salts are found, for example, in Remington's Pharmaceutical Sciences, 20th ed., Lippincott Williams & Wilkins, Baltimore, Md., 2000, p. 704. Examples of ophthalmic drugs sometimes administered in the form of a pharmaceutically acceptable salt include timolol maleate, brimonidine tartrate, and sodium diclofenac.

In some cases, the active agent is a diagnostic agent imaging or otherwise assessing the eye. Exemplary diagnostic agents include paramagnetic molecules, fluorescent compounds, magnetic molecules, and radionuclides, x-ray imaging agents, and contrast media.

In certain embodiments, the pharmaceutical composition contains one or more local anesthetics. Representative local anesthetics include tetracaine, lidocaine, amethocaine, proparacaine, lignocaine, and bupivacaine. In some cases, one or more additional agents, such as a hyaluronidase enzyme, is also added to the formulation to accelerate and improves dispersal of the local anesthetic.

V. Methods of Use

There are several types of glaucoma. The two main types are open-angle and angle-closure. These are marked by an increase of intraocular pressure (TOP), or pressure inside the eye.

Open-angle glaucoma, the most common form of glaucoma, accounting for at least 90% of all glaucoma cases, is caused by the slow clogging of the drainage canals, resulting in increased eye pressure. It has a wide and open angle between the iris and cornea, develops slowly and is a lifelong condition, and has symptoms and damage that are not noticed. "Open-angle" means that the angle where the iris meets the cornea is as wide and open as it should be. Open-angle glaucoma is also called primary or chronic glaucoma. It is the most common type of glaucoma, affecting about three million Americans.

Angle-closure glaucoma, a less common form of glaucoma: It is caused by blocked drainage canals, resulting in a sudden rise in intraocular pressure, has a closed or narrow angle between the iris and cornea, develops very quickly, has symptoms and damage that are usually very noticeable, and demands immediate medical attention. It is also called acute glaucoma or narrow-angle glaucoma. Unlike open-angle glaucoma, angle-closure glaucoma is a result of the angle between the iris and cornea closing.

Normal-Tension Glaucoma (NTG) or low-tension or normal-pressure glaucoma is where the optic nerve is damaged even though the eye pressure is not very high. Congenital Glaucoma occurs in babies when there is incorrect or incomplete development of the eye's drainage canals during the prenatal period. This is a rare condition that may be inherited. When uncomplicated, microsurgery can often correct the structural defects. Other cases are treated with medication and surgery. Other Types of Glaucoma include: Secondary Glaucoma, Pigmentary Glaucoma, Pseudoexfoliative Glaucoma, Traumatic Glaucoma, Neovascular Glaucoma, Irido Corneal Endothelial Syndrome (ICE), and Uveitic Glaucoma.

Open angle glaucoma is the most common form of glaucoma, affecting about three million Americans. It happens when the eye's drainage canals become clogged over time. The inner eye pressure (intraocular pressure or IOP) rises because the correct amount of fluid cannot drain out of the eye. With open-angle glaucoma, the entrances to the drainage canals are clear and should be working correctly. If open-angle glaucoma is not diagnosed and treated, it can cause a gradual loss of vision. This type of glaucoma develops slowly and sometimes without noticeable sight loss for many years. It usually responds well to medication, especially if caught early and treated.

Vision loss in glaucoma, a neurodegenerative disease that is the leading cause of irreversible blindness worldwide, is due to the dysfunction and death of retinal ganglion cells (RGCs). Current therapies all act by lowering intraocular pressure (TOP). However, pressure reduction can be difficult to achieve, and even with significant pressure lowering, RGC loss can continue. Efforts have therefore been made to develop neuroprotective agents that would complement IOP-lowering by directly inhibiting the RGC cell death process, though no neuroprotective agent is yet in clinical use.

As described in the examples, using a high-content phenotypic screen based on primary RGC cultures, it was unexpectedly found that the FDA-approved drug sunitinib strongly promotes RGC survival in rodent glaucoma and traumatic optic neuropathy models. In order to identify the molecular target(s) through which sunitinib promotes RGC survival, a high-throughput RNA interference-based assay was developed, and used to screen the full mouse kinome. The screen identified dual-leucine zipper kinase (DLK) as a key neuroprotective drug target of sunitinib. Supporting this finding, a number of other neuroprotective kinase inhibitors also inhibit DLK. These include SR8165, axitinib, bosutinib, neratininb, crizotinib, tozasertib, lestautinib, foretinib, TAE-684 and KW-2449.

Although described herein primarily with respect to sunitinib, it is understood that these other compounds could be used in place of sunitinib. Furthermore, it was shown that DLK undergoes a robust post-transcriptional upregulation in response to injury that is both necessary and sufficient for RGC cell death. Together, the results establish a drug/drug target combination in glaucoma, suggest a possible biomarker for RGC injury, and provide a starting point for the development of more specific neuroprotective DLK inhibitors for the treatment of glaucoma and other forms of optic nerve disease.

The formulations provide for more sustained controlled release of sunitinib and similar compounds for reduction or prevention of neuronal death due to elevated intraocular pressure associated with glaucoma. Upon administration, the sunitinib or other agents are released over an extended period of time at concentrations which are high enough to produce therapeutic benefit, but low enough to avoid cytotoxicity.

When administered to the eye, the particles release a low dose of one or more active agents over an extended period of time, preferably longer than 3, 7, 10, 15, 21, 25, 30, or 45 days. The structure of the drug or makeup of the polymeric matrix, particle morphology, and dosage of particles administered can be tailored to administer a therapeutically effective amount of one or more active agents to the eye over an extended period of time while minimizing side effects, such as the reduction of scoptopic ERG b-wave amplitudes and/or retinal degeneration.

Pharmaceutical compositions containing particles for the controlled release can be administered to the eye of a patient in need thereof to treat or prevent one or more diseases or disorders of the eye. In some cases, the disease or disorder of the eye affects the posterior segment of the eye. The posterior segment of the eye, as used herein, refers to the back two-thirds of the eye, including the anterior hyaloid membrane and all of the optical structures behind it, such as the vitreous humor, retina, choroid, and optic nerve.

1. Methods of Administration

The formulations described herein can be administered locally to the eye by intravitreal injection (e.g., front, mid or back vitreal injection), subconjunctival injection, intracameral injection, injection into the anterior chamber via the temporal limbus, intrastromal injection, injection into the subchoroidal space, intracorneal injection, subretinal injection, and intraocular injection. In a preferred embodiment, the pharmaceutical composition is administered by intravitreal injection.

The implants described herein can be administered to the eye using suitable methods for implantation known in the art. In certain embodiments, the implants are injected intravitreally using a needle, such as a 22-gauge needle. Placement of the implant intravitreally may be varied in view of the implant size, implant shape, and the disease or disorder to be treated.

In some embodiments, the pharmaceutical compositions and/or implants described herein are co-administered with one or more additional active agents. "Co-administration", as used herein, refers to administration of the controlled release formulation of one or more Drugs with one or more additional active agents within the same dosage form, as well as administration using different dosage forms simultaneously or as essentially the same time. "Essentially at the same time" as used herein generally means within ten minutes, preferably within five minutes, more preferably within two minutes, most preferably within in one minute.

In some embodiments, the pharmaceutical compositions and/or implants described herein are co-administered with one or more additional treatments for a neovascular disease or disorder of the eye. In some embodiments, the pharmaceutical compositions and/or implants described herein are co-administered with one or more anti-angiogenesis agent such bevacizumab (AVASTIN®), ranibizumab, LUCENTIS®, or aflibercept (EYLEA®).

b. Dosage

Preferably, the particles will release an effective amount of sunitinib over an extended period of time. In preferred embodiments, the particles release an effective amount of sunitinib over a period of at least two weeks, more preferably over a period of at least four weeks, more preferably over a period of at least six weeks, most preferably over a period of at least eight weeks. In some embodiments, the particles release an effective amount of sunitinib over a period of three months or longer to reduce or prevent neuronal cell death, especially that of the optic nerve due to elevated intraocular pressure.

Although described with reference to reference to the eye, it is understood that the formulation may be administered to other sites to protect neuronal cells, including the brain.

The present invention will be further understood by reference to the following non-limiting examples.

Example 1. Preparation of Sunitinib-Encapsulated Microparticles and In Vitro Characterizations Materials and Methods Preparation of Sunitinib-Encapsulated Microparticles Polymer microparticles of PLGA and/or a diblock copolymer of PLGA and PEG covalently conjugated to PLGA ($M_w$ 45 kDa) (PLGA45k-PEG5k) with or without sunitinib malate were prepared using a single emulsion solvent evaporation method. Briefly, PLGA and/or PLGA-PEG were first dissolved in dichloromethane (DCM) and sunitinib malate was dissolved in dimethyl sulfoxide (DMSO) at predetermined concentrations. The polymer solution and the drug solution were mixed to form a homogeneous solution (organic phase). The organic phase was added to an aqueous solution of 1% polyvinyl alcohol (PVA) (Polysciences, Mw 25 kDa, 88% hydrolyzed) and homogenized at 5,000 rpm for 1 min using an L5M-A laboratory mixer (Silverson Machines Inc., East Longmeadow, Mass.) to obtain an emulsion.

The solvent-laden microparticles in the emulsion was then hardened by stirring at room temperature for >2 hr to allow the DCM to evaporate. The microparticles were collected by sedimentation and centrifugation, washed three times in water and dried by lyophilization.

Both cationic and ionic surfactants, Sodium dodecyl sulfate ("SDS") and Hexadecyltrimethylammonium ("HDTA"), were added to the solvents to make the particles. These were substituted with a non-ionic solvent, polyvinyl alcohol ("PVA"). Sunitinib free base crystallized and could not be utilized. DMSO was added to the solvent, alone and in combination with surfactant.

The particles were collected by centrifugation, washed, and freeze-dried to a powder to be reconstituted prior to administration. Average particle size and size distribution was determined using a Coulter Multisizer. Drug release kinetics in infinite sink conditions at 37° C. in PBS and vitreous solution mimic were determined.

Determination of Drug Loading

Drug loading was determined by UV-Vis spectrophotometry. Microparticles containing sunitinib (10 mg total weight) were dissolved in anhydrous DMSO (1 mL) and further diluted until the concentration of drug was in the linear range of the standard curve of UV absorbance of the drug. The concentration of the drug was determined by comparing the UV absorbance to a standard curve. Drug loading is defined as the weight ratio of drug to microparticles.

In Vitro Drug Release

Microparticles containing sunitinib (10 mg total weight) were suspended in 4 mL of PBS containing 1% TWEEN® 20 in a 6-mL glass vial and incubated at 37° C. under shaking at 150 rpm. At predetermined time points, 3 mL of the supernatant was withdrawn after particles settled to the bottom of the vial and replaced with 3 mL of fresh release medium. The drug content in the supernatant was determined by UV-Vis spectrophotometry or HPLC.

Measurement of Average Size and Size Distribution of Microparticles

Several milligrams of the microparticles were first suspended in water and dispersed in an ISOTON® diluent. The mean particle size and distributions were determined using a COULTER MULTISIZER IV (Beckman Coulter, Inc., Brea, Calif.).

Results

Both cationic and ionic surfactants, such as Sodium dodecyl sulfate ("SDS") and Hexadecyltrimethylammonium ("HDTA"), were added to the solvents to make the particles. Loadings were extremely low (0.20% with SDS and 0.27% with HDTA). Substituting a non-ionic solvent such as polyvinyl alcohol ("PVA") increased loading, up to 1.1%. Sunitinib free base crystallized and could not be utilized to obtain higher loading. Using DMSO increased loading even more so, up to around 5%.

TABLE 1

Composition and process parameters of sunitinib-encapsulated polymer microparticle formulations

| Formulation ID | Organic phase | | | | | | Aqueous phase | | Emulsion rat (rpm) | Drug loading (wt %) | Target loading (wt %) | Encapsulation efficier |
|---|---|---|---|---|---|---|---|---|---|---|---|---|
| | PLGA (mg) | PLGA type | PLGA 5050 PEG 5 kD (10% PEG by wt) (mg) | DCM (mL) | Sunitinib malate (mg) | DMSO (mL) | Surfactant | Volume (mL) | | | | |
| DC-2-55-2 | 560 | 7525 4A | 5.6 | 4 | 90 | 2 | 1% PVA in pH 4 buffer | 200 | 5000 | 3.1 | 13.7 | 22.6 |
| DC-2-55-3 | 560 | 7525 4A | 5.6 | 4 | 90 | 2 | 1% Borate Buffer (pH 10) | 200 | 5000 | NA | 13.7 | NA |
| DC-2-55-4 | 560 | 7525 4A | 5.6 | 4 | 90 | 2 | 1% PVA in H2O (pH 6) | 200 | 5000 | 5.0 | 13.7 | 36.4 |
| DC-2-55-5 | 560 | 7525 4A | 5.6 | 4 | 90 | 2 | 1% PVA in PBS (pH 7.4) | 200 | 5000 | 11.5 | 13.7 | 83.8 |
| DC-2-50-1 | 800 | 7525 4A | 8 | 4 | 145 | 2 | 1% PVA in PBS | 200 | 5000 | 13.9 | 15.2 | 91.4 |
| DC-2-50-2 | 560 | 7525 4A | 5.6 | 4 | 100 | 2 | 1% PVA in PBS | 200 | 5000 | 12 | 15.0 | 79.9 |
| DC-2-50-3 | 400 | 7525 4A | 4 | 4 | 70 | 2 | 1% PVA in PBS | 200 | 5000 | 7.8 | 14.8 | 52.8 |
| DC-2-50-4 | 280 | 7525 4A | 2.8 | 4 | 50 | 2 | 1% PVA in PBS | 200 | 5000 | 6.8 | 15.0 | 45.3 |
| DC-2-50-5 | 200 | 7525 4A | 2 | 4 | 35 | 2 | 1% PVA in PBS | 200 | 5000 | 4.9 | 14.8 | 33.2 |
| DC-1-53-1 | 400 | 7525 6E | 4 | 4 | 160 | 2 | 1% PVA in PBS | 200 | 5000 | 23.7 | 28.4 | 83.6 |
| DC-1-53-2 | 400 | 8515 6E | 4 | 4 | 160 | 2 | 1% PVA in PBS | 200 | 5000 | 23.9 | 28.4 | 84.1 |
| DC-1-53-3 | 400 | 8515 6A | 4 | 4 | 160 | 2 | 1% PVA in PBS | 200 | 5000 | 22.6 | 28.4 | 79.6 |
| JCK--1-72-1 | 400 | 5050 2A | | 8 | 80 | 2 | 1% PVA in H2O | 200 | 4000 | 3.4 | 16.7 | 20.1 |
| YY-1-59-1 | 200 | 7525 4A/7525 1.5A (1:1) | 2 | 3 | 40 | 1 | 1% PVA in PBS | 100 | 4000 | 6.8 | 16.5 | 41.2 |
| YY-1-83-1 | 554 | 7525 4A | 6 | 4 | 160 | 2 | 1% PVA in PBS | 200 | 5000 | 20.5 | 22.2 | 92.2 |
| YY-1-83-2 | 504 | 7525 4A | 56 | 4 | 160 | 2 | 1% PVA in PBS | 200 | 5000 | 20.2 | 22.2 | 90.7 |
| YY-1-93-1 | 400 | 7525 4A | 4 | 4 | 90 | 2 | 1% PVA in PBS | 200 | 4000 | 12.4 | 18.2 | 68.1 |
| YY-1-93-2 | 560 | 7525 4A | 5.6 | 4 | 90 | 2 | 1% PVA in PBS | 200 | 5000 | 11.6 | 13.7 | 84.5 |
| YY-1-96-1 | 2240 | 7525 4A | 22.4 | 16 | 360 | 8 | 1% PVA in PBS | 800 | 3000 | 10.1 | 13.7 | 73.6 |
| JCK-1-26-8 | 100 | 7525 6E | | 2 | 75 | 1 | 1% PVA in PBS | 100 | 4000 | 34.5 | 42.9 | 80.5 |

Example 2. The Effect of Aqueous pH on Encapsulation Efficiency of Sunitinib Materials and Methods As the solubility of sunitinib in aqueous solution was shown to be pH dependent, microparticle formulations encapsulating sunitinib were prepared in aqueous phases of various pH values to investigate the effect of aqueous pH on drug encapsulation.

Results

As shown in Table 2, the loading and encapsulation efficiency increased significantly when the aqueous pH was increased from 4 to 7.4. However, when the pH was adjusted to 10 and the aqueous solution became more basic, the morphology of many particles changed from spherical to irregular shapes and some particles formed aggregates, suggesting aqueous solution of high pH is also unfavorable for producing particles of high loading of sunitinib and high quality.

TABLE 2

The effect of aqueous phase pH on encapsulation efficiency of sunitinib

| Sample ID | Aqueous pH | Actual loading | Target loading | Encapsulation efficiency | Mean diameter (μm) |
|---|---|---|---|---|---|
| DC-2-55-2 | 4 | 3.1% | 13.7% | 22% | 27.0 ± 7.9 |
| DC-2-55-4 | 6 | 5.0% | 13.7% | 36% | 28.0 ± 8.3 |
| DC-2-55-5 | 7.4 | 11.5% | 13.7% | 84% | 27.4 ± 7.6 |
| DC-2-55-3 | 10 | NA | 13.7% | NA | NA |

Example 3: Testing of Sunitinib for Glaucoma Treatment

Materials and Methods

Reagents

Sunitinib, lestaurtinib, crizotinib, axitinib, bosutinib, imatinib, tandutinib, vandetanib, sorafenib and vatalanib were purchased from LC labs, Forentinib, KW-2449 from Selleckchem, and tozasertib from Biovision life science.

PLGA Microspheres

Polymer microparticles loaded with sunitinib, SR8165, or tozasertib were prepared using a single emulsion solvent evaporation method. Briefly, a solution was made by mixing 200 mg of poly(lactic-co-glycolic acid) (PLGA 50:50, 2A, 0.15-0.25 dL/g, MW15K-17K, Lakeshore Biomaterials, Birmingham, Ala.) dissolved in 4 mL methylene chloride with one of various drugs dissolved in DMSO (40 mg sunitinib in 1 mL DMSO, 40 mg SR8165 in 0.5 mL DMSO, 40 mg tozasertib in 1 mL DMSO). The mixture was homogenized at 4000 rpm (Silverson Homogenizer, model L4RT, Chesham Bucks, England) for 1 min into an aqueous solution containing 1% polyvinyl alcohol (PVA, MW=25 KDa, Polysciences, Warrington, Pa.). The particles were then stirred for 2 hours to allow hardening, collected by centrifugation at 5000 g for 5 minutes, washed with deionized water 3 times, and freeze-dried to a powder that could be reconstituted prior to administration. Microparticle size was determined using a Coulter Multisizer IIe (Beckman-Coulter Inc., Fullerton, Calif.). To determine the drug release rate in vitro, 5 mg of drug-loaded particles were suspended in 2 mL of phosphate-buffered saline (pH 7.4) and incubated at 37° C. on a rotator. At selected time points, microparticles were precipitated by centrifugation, and the supernatant removed and replaced with 2 mL of fresh phosphate buffer. Supernatants were analyzed by spectrophotometry at 420 nm for sunitinib and SR8165, and 252 nm for tozasertib.

Statistical Analysis

All statistical analyses were performed with the unpaired Mann-Whitney-Wilcoxon test.

RGC Purification, Culture, Screening and Imaging

All animal use was in accordance with ARVO Statement for the Use of Animals, and all the experimental procedures were performed in compliance with animal protocols approved by the IACUC at Johns Hopkins University. Retinas were isolated from postnatal 0-5 day mice and dissociated with papain. Microglia was immunodepleted with anti-CD11b conjugated Dynabeads. The suspension of retinal cells were immunopanned on plates pre-conjugated with anti-Thy1.2 antibody (Serotec, MCA028) and anti-mouse IgM at room temperature (RT). After washing, RGCs were released from the plate by a cell lifter, counted, and seeded at a density of 10,000 per well in 96-well plates in the media composed of Neurobasal, B27, N2 supplement, L-glutamine, and penicillin/streptomycin. After a 72 hour culture at 37° C., RGCs were stained with calcein AM, ethidium homodimer, and Hoechst 33342. Images were taken from portions of each well with Cellomics Kinetscan, and cell survival was quantified and calculated with the algorithms in Cellomics Neuroprofiling package. As indicated, RGC viability was alternatively measured by CellTiter-Glo luminescence (Promega).

For siRNA-based screening, the siRNAs from the Sigma Mission Mouse Kinome library were complexed with NeuroMag (Oz Biosciences) at a final concentration of 20 nM. RGCs were then reverse transfected on a stationary magnet and assayed for survival 72 hours later. Oligonucleotides conferring survival more than 3 SD from the nontargeting siRNAs were considered neuroprotective (106 siRNA, 5.4%). Confirmatory siRNAs were obtained from both Dharmacon and Ambion. For small molecule-based screening, serially diluted compounds in DMSO were transferred to 1536 well assay plates by a 23 nL pintool array (Kalypsys, San Diego, Calif.), with a final concentration of 0.057% DMSO for each respective compound concentration. RGCs were cultured for 48 h, and cell viability was analyzed on a plate reader (ViewLux, Perkin Elmer) using the bioluminescent CellTiterGlo (Promega) assay. Concentration response curves were created using CurveFit (NIH NCATS). The screened libraries include the modified Tocriscreen (1395 compounds) collection, FDA-approved drugs (2814 compounds), LOPAC (1208 compounds) and PTL2/PTL3 (based on pteridin, pyrimidine and quinazoline scaffolds; 2319 compounds).

Rat Intravitreal Injections 6-week old male Wistar rats were anesthetized with ketamine/xylazine. A partial peritomy was made to expose the sclera. The injection site was approximately 1 mm posterior to the ora serrata, and the injection glass pipet was angled towards the optic disc in order to avoid lens injury. 5 μL (10 μg) of PLGA microspheres were injected with a glass pipet and Hamilton syringe.

Rat Optic Nerve Transection

The optic nerve was exposed by a partial peritomy and intraorbital dissection of the extraocular muscles, and then transected with a 25-gauge needle. 4-Di-10-ASP were then applied to the proximal nerve stump. Care was taken to avoid vascular injury during the transection, and retinal perfusion was examined after nerve transection. Two weeks after transection, rats were sacrificed and enucleated. Retinas were flatmounted, imaged with confocal microscopy and the number of 4-Di-10-ASP-labeled cells with RGC morphology was quantified. Imaging and quantification of RGC survival were performed in a masked fashion.

Rat Laser-Induced Ocular Hypertension

Intraocular pressure (TOP) was unilaterally elevated by laser treatment of the trabecular meshwork as previously described[7]. Briefly, 6-week old Wistar male rats were anesthetized with ketamine/xylazine. On two consecutive weeks, 40-50 532 nm diode laser spots were applied to the prelimbal region (50 μm diameter, 600 mW power and 0.6 seconds duration). Under anesthesia, the IOP of laser-treated and fellow eyes was measured with TonoLab one and three days after laser treatment. Four weeks following laser treatment, rats were perfused with 4% paraformaldehyde in phosphate buffer. Optic nerves were isolated, postfixed with 1% osmium tetroxide, embedded in epoxy resin and stained with 1% toluidine blue. Images from 10 random and nonoverlapping fields were taken with 100× oil phase contrast objective. The area of entire optic nerve cross-sections were imaged with 10× magnification, and used with axon counts from the 10 field to derive axon counts per nerve. The laser treatment and acquisition of optic nerve images were performed in a masked fashion.

Mouse Intravitreal Injection and Optic Nerve Crush 3-month old male C57BL/6 and Dlk floxed mice (BL/6 background) were anesthetized with ketamine/xylazine and intravitreally injected with $10^{10}$ DNA-containing particles of capsid-mutant (Y444, 500, 730F) AAV2 expressing Cre recombinase from the chicken β-actin promoter. 7 days later, optic nerve was surgically exposed and crushed with Dumont N5 self-closing forceps 1 mm behind the globe for 3 seconds. 10 days following nerve crush, eyes were enucleated, fixed and RGC survival was measured with flatmount immunostaining for βIII-tubulin and Brn3. Intravitreal injection, optic nerve crush, immunofluorescence and RGC counting were performed in a masked fashion.

Western Blots, Immunofluorescence and RT-PCR

Western blots were performed according to the standard protocol. The following antibodies were from Cell Signaling Technology: Phospho-JNK, Thr183/Tyr185 (4671); JNK (9258); Phospho-MKK7 (4171), and MKK7 (4172). Monoclonal anti-alpha-tubulin antibody (T6074) was purchased from Sigma. DLK rabbit polyclonal was provided by S. Hirai.

Retinal immunofluorescence was performed following standard protocols. The following antibodies were used: mouse neuronal class βIII tubulin (clone TUJ1, 1:500, Covance), rabbit polyclonal anti-DLK (1:200, S. Hirai), and goat polyclonal Brn3 (C-13, 1:100), rabbit anti-Cre (1:100, Novus).

Dlk mRNA levels were measured with RT-PCR with the following primer set: 5'-ATTCCTCAGCCATCATCTGG-3' (SEQ ID NO:1) and 5'-ATTTCGTGGTTTGCTGTTCC-3' (SEQ ID NO:2).

Electrophysiology

Recordings were made by using the whole-cell patch-clamp technique in both current- and voltage-clamp modes with an Axopatch 200B. Data were low-pass filtered at 1 kHz (Bessel) and sampled at 10 kHz. A liquid junction potential of −2 mV has been corrected, and the resting potential was estimated to be −62±2.2 mV (Mean±SEM, n=13). The recording pipette was filled with the following intracellular solution (in mM): 100 K-gluconate, 50 KCl, 20 HEPES, 10 EGTA, 5 $MgCl_2$, 2 ATP, 0.1 GTP, pH adjusted to 7.33 with KOH. The cells were continuously perfused with (in mM): 140 NaCl, 5 KCl, 1 $MgCl_2$, 2.5 $CaCl_2$, 10 glucose, 10 HEPES, pH 7.4 with NaOH.

Production of AAV Vectors

AAV vector preparations are produced by the 2-plasmid, co-transfection method with modifications[23]. Briefly, ~$10^9$ HEK 293 cells is cultured in DMEM with 5% fetal bovine serum and antibiotics. DNA transfection of the two vector plasmids by CaPO4 precipitation then is allowed to incubate at 37° C. in 7% $CO_2$ for 60 h. The cells are then harvested, lysed by three freeze/thaw cycles, the crude lysate clarified by centrifugation and the resulting vector-containing supernatant run on a discontinuous iodixanol step gradient. The vector-containing fraction is further purified and concentrated by column chromatography on a 5-ml HiTrap Q Sepharose column using a Pharmacia AKTA FPLC system. The vector is eluted from the column using 215 mM NaCl, pH 8.0, and the AAV peak collected, concentrated and buffer exchanged into Alcon BSS with 0.014% Tween 20. Before release, vector purity is assessed by silver-stained SDS-PAGE, a negative bioburden test, and an endotoxin test in the acceptable range. Finally, vector is titered for DNase-resistant vector genomes by Real-Time PCR relative to a reference AAV vector standard.

Results

High-Content, High-Throughput, Phenotypic Screen

Screening over 6,000 unique compounds at multiple doses[5] repeatedly identified sunitinib and related oxindole analogs as being highly neuroprotective. Sunitinib treatment led to a dose-dependent increase in the viability of primary RGCs, with maximal activity between 0.5 and 1 μM (FIG. 1A). Increased survival was associated with a corresponding decrease in markers of apoptosis, including caspase activation, nuclear condensation and fragmentation.

Rescue of RGC Death in Response to Optic Nerve Transection

Figure 1B:
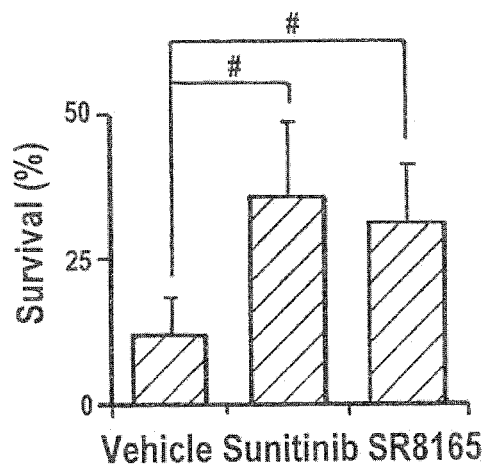
FIG. 1B graphs percent survival of RGCs after optic nerve transection in rats pretreated with intravitreal drug-eluting microspheres containing vehicle (n=10), 440 ng sunitinib (n=6) or 300 ng SR8165 (n=10).
Figure 1C:
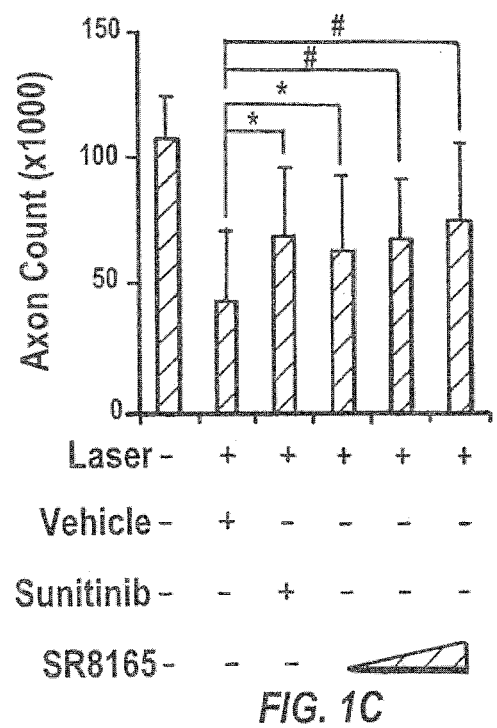
FIG. 1C is a graph showing optic nerve axon counts following laser-induced ocular hypertension in rats pretreated with intravitreal microspheres containing vehicle (n=29), 440 ng sunitinib (n=8) or 100 ng (n=24), 300 ng (n=26) or 600 ng (n=25) SR8165.
Figure 2A:
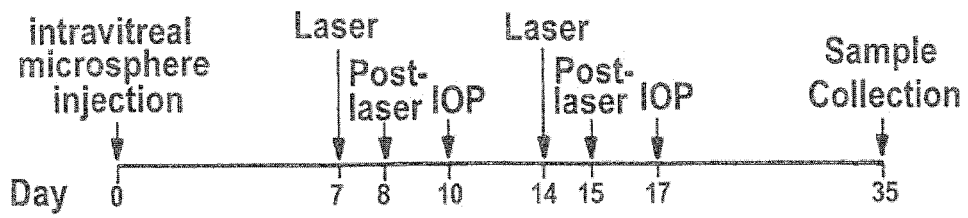
FIG. 2A is a schematic of laser induced ocular hypertension in a rat glaucoma model.
Figure 2B:
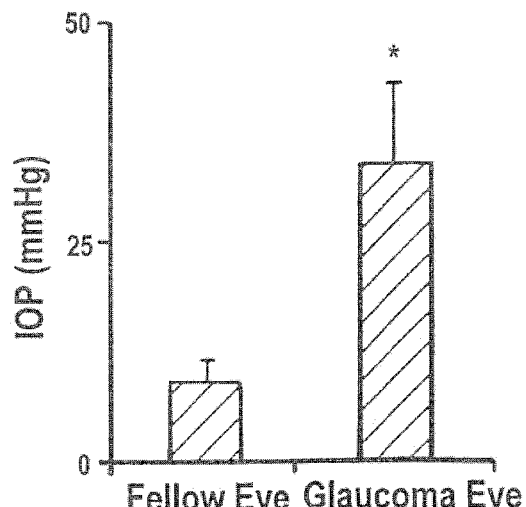
FIG. 2B is a graph of Mean IOP increase 24 hours after the first administration of diode laser to the trabecular meshwork.
Figure 2C:
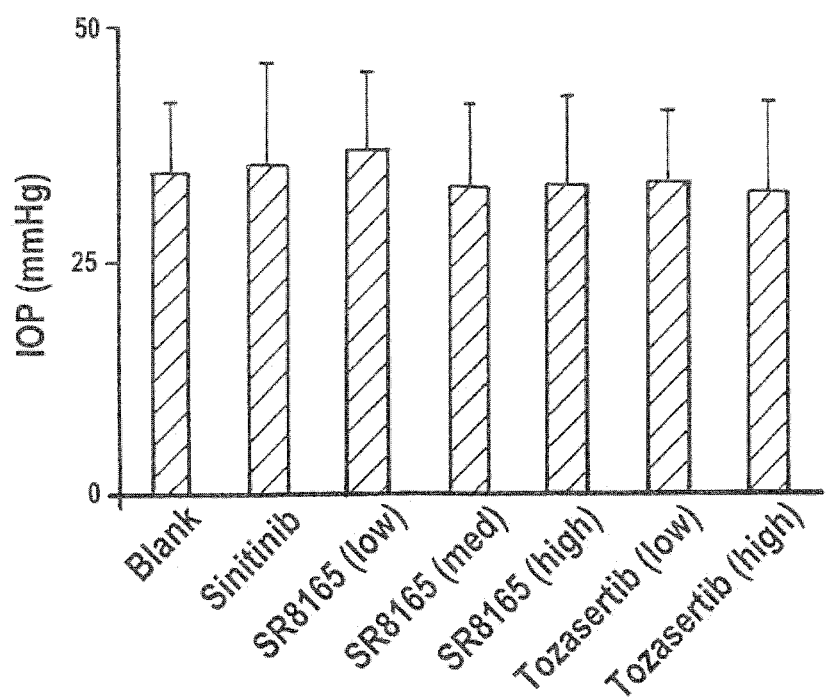
FIG. 2C is a graph of IOP 24 hours after the first administration of diode laser, divided by treatment group.
Figure 3A:
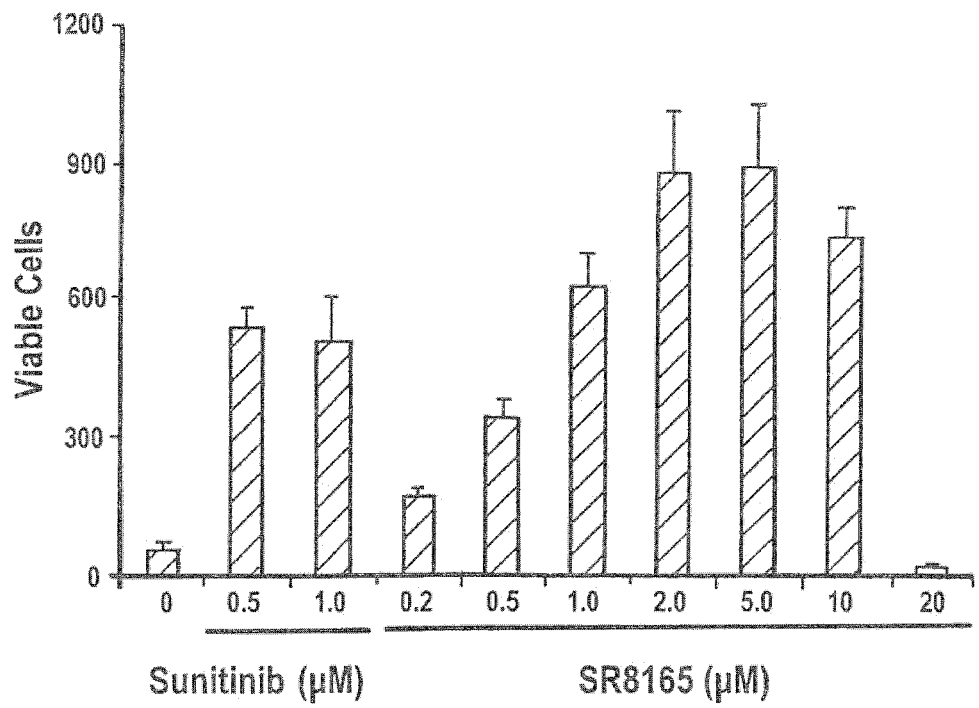
FIG. 3A is a graph of viable cells showing survival of immunopanned RGCs, treated with increasing doses of SR8165, after 72 hours in culture. The most efficacious doses of sunitinib are shown for comparison.
Figure 3B:
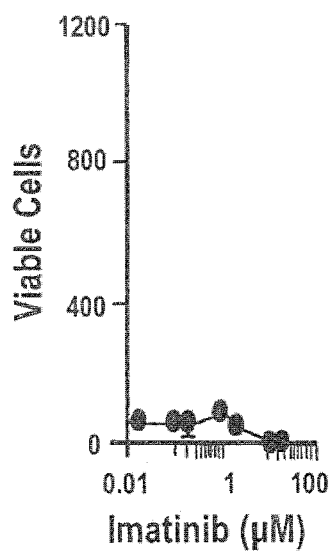
FIGS. 3B-3F are graphs of viable cells, showing the lack of neuroprotective activity of kinase inhibitors targeting VEGFR2, c-Kit, FLT3 and PDGFRs, of immunopanned RGCs, treated with increasing doses of the various kinase inhibitors, after 72 hours in culture.
Figure 3C:
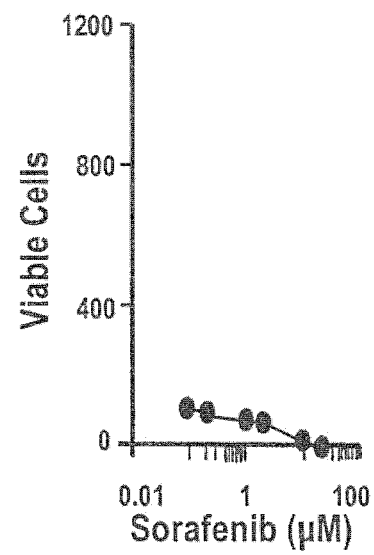
Figure 3D:
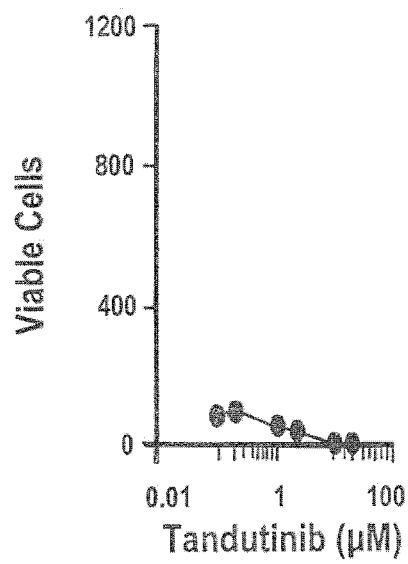
Figure 3E:
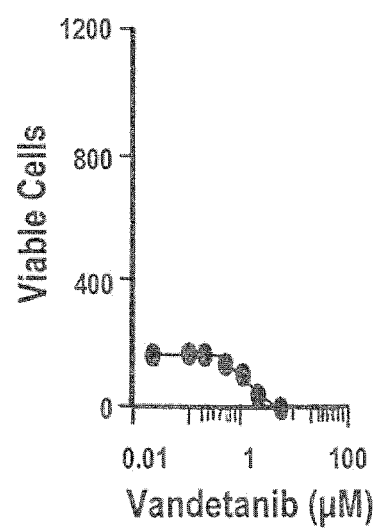
Figure 3F:
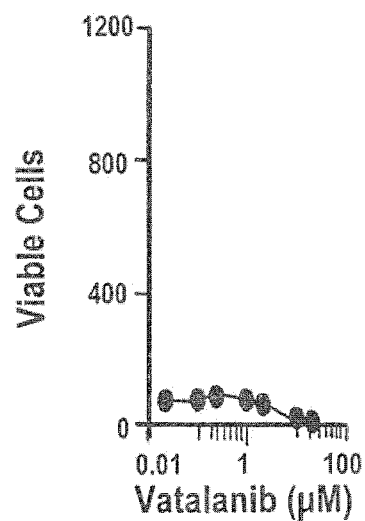

The ability of sunitinib to rescue RGC death in vivo in response to optic nerve transection was tested. Sunitinib, or its vehicle control were packaged in poly(lactic-co-glycolic acid) (PLGA)-based, slow-eluting microspheres and injected intravitreally into Wistar rats. Seven days later, optic nerves were transected and RGCs were retrogradely-labeled by applying 4-Di-10-ASP to the proximal nerve stump. At two weeks post-transection, sunitinib-treated compared to control animals showed a 3-4 fold increase in surviving RGCs (FIG. 1B). To evaluate sunitinib's neuroprotective activity in a glaucoma model, rats were pretreated with intravitreal vehicle- or sunitinib-eluting microspheres and then used diode laser treatment of the trabecular meshwork to increase IOP (FIGS. 2A-2C). In eyes injected with control microspheres, there was a 58% reduction in optic nerve axons at one month. However, in eyes treated with sunitinib-eluting microspheres, axon loss was reduced by 40% (p<0.05, FIG. 1C). SR8165, a sunitinib-analog found to have greater efficacy in vitro (FIG. 5A), conferred similar neuroprotection upon delivery from PLGA microspheres (FIG. 1C). Together, these results establish sunitinib, and related oxindole analogs, as neuroprotective agents for glaucoma.

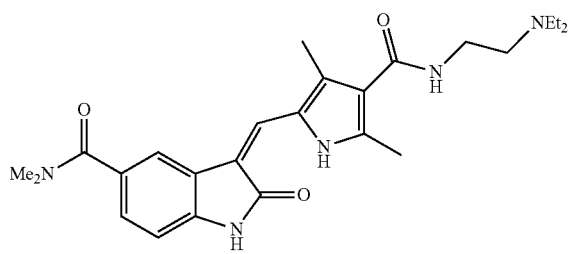

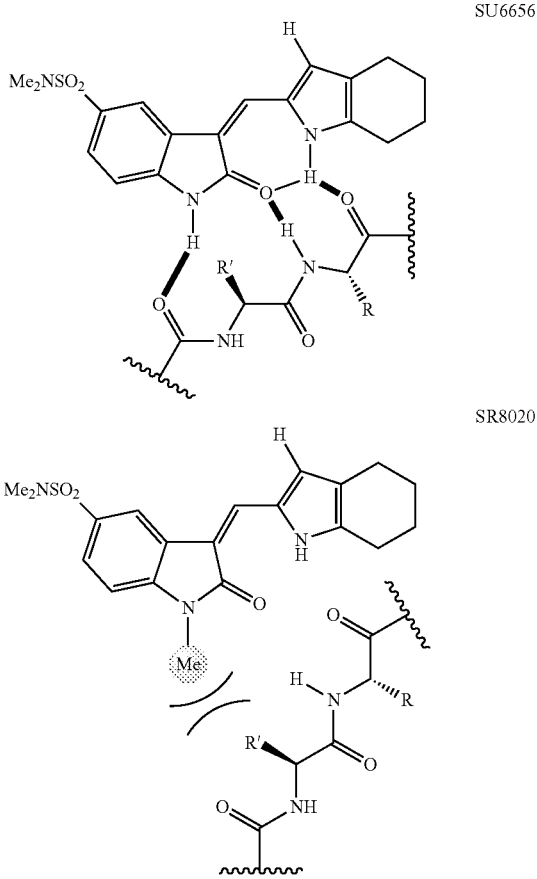

To confirm that kinase inhibition mediated the neuroprotective activity of these oxindole kinase inhibitors, the activity of SU6656, a neuroprotective analog of sunitinib, was compared to that of SR8020, an otherwise identical derivative in which a hydrogen to methyl group substitution is predicted to disrupt the binding to the kinase ATP-binding pocket. SR8020 failed to show survival-promoting activity, thus suggesting that the neuroprotective activity of sunitinib and its analogs is mediated through ATP-competitive kinase inhibition. At neuroprotective concentrations, sunitinib inhibits nearly 200 kinases.

TABLE 3

Particle Size, Loading, Release

| | Particle Size (μm) | Drug Loading (wt. drug/total wt.) | Drug Release Rate (μg drug/mg particles) |
|---|---|---|---|
| Sunitinib | 9.1 ± 1.4 | 11.0 | 2.5 |
| SR8165 | 10.4 ± 1.7 | 11.0 | 6.5 |
| Tozasertib | 11.2 ± 1.5 | 5.5 | 0.6 |

Among the kinases potently inhibited are vascular endothelial growth factor receptor 2 (VEGFR2), c-Kit, FLT3 and platelet-derived growth factor receptors (PDGFRs). However, other small molecules known to inhibit one or more of those same receptor tyrosine kinases, including imatinib, sorafenib, tandutinib, vandetanib, and vatalanib, all lack neuroprotective activity (FIGS. 3B-3F). These results, together with the relatively high concentrations required for neuroprotection in vitro, suggested that the kinase(s) whose inhibition promotes RGC survival are one or more low-affinity targets of sunitinib. In order to identify the relevant kinase(s), the primary RGC platform was adapted for an unbiased RNA interference-based screen of the entire mouse kinome. It was reasoned that kinases, whose knockdown increased RGC survival, would represent possible relevant targets for neuroprotective kinase inhibition. Since traditional transfection procedures resulted in minimal RGC transfection, or were toxic, a magnetic nanoparticle-based high-throughput method was developed that provided efficient siRNA delivery to cultured primary RGCs. An arrayed library of 1869 siRNAs was then screened against 623 kinases, providing three-fold coverage of the mouse kinome.

The only two kinases for which all three siRNAs were significantly neuroprotective were mitogen-activated protein kinase kinase kinase 12/dual-leucine zipper kinase (Map3k12/Dlk) and its only known substrate, mitogen-activated protein kinase kinase 7 (Map2k7/Mkk7). Involvement of both kinases was subsequently confirmed in secondary screening using an independent set of siRNAs. MKK7 and its homolog, MKK4, are the canonical activators of the c-Jun N-terminal kinases (JNK1-3), key mediators of RGC cell death. The results indicate that DLK may be the as-yet-unidentified trigger for JNK activation and cell death in RGCs. Indeed, DLK has been shown to mediate developmental apoptosis in peripheral motor and sensory neurons, but no role in adult CNS neurodegenerations has been firmly established.

Figure 4A:
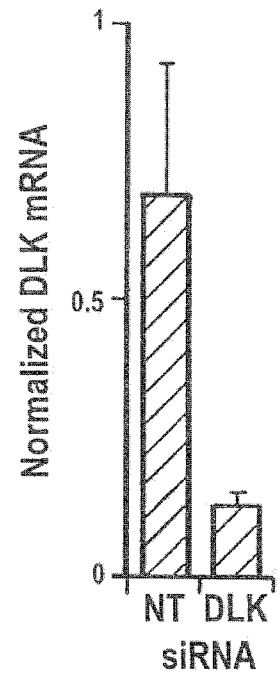
FIG. 4A is a graph of knockdown of DLK mRNA and protein by DLK siRNA. RGCs were transfected with DLK or a nontargeting control (NT) siRNA. mRNA levels were quantified at 24 hours using RT-PCR.
Figure 4B:
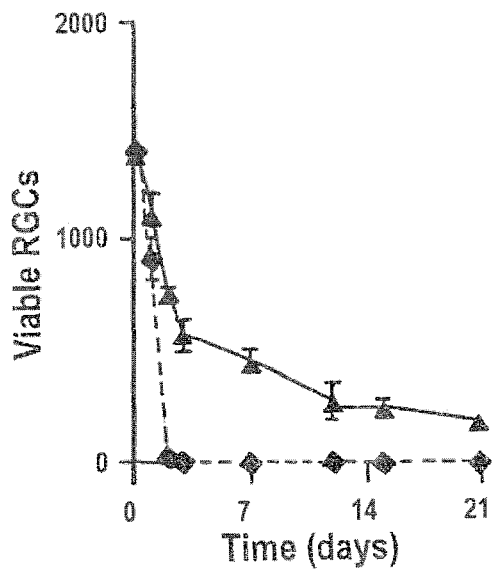
FIG. 4B is a graph showing survival of immunopanned RGCs transfected with control (dashed) or DLK siRNA (solid).
Figure 4C:
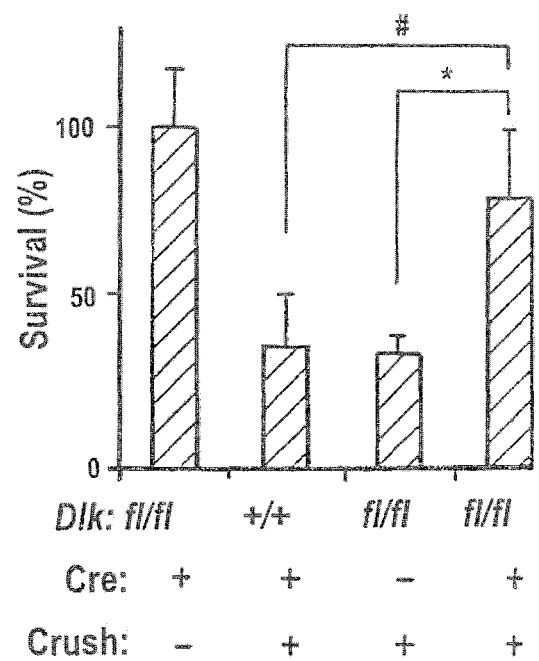
FIG. 4C is a graph of percent survival of RGCs 10 days after optic nerve crush in $Dlk^{fl/fl}$ mice (n=3), $Dlk^{fl/fl \ a}$ mice injected with AAV2-Cre (n=8) or $Dlk^{+/+}$ mice injected with AAV2-Cre (n=9), normalized to uninjured control mice (n=6).
Figure 4D:
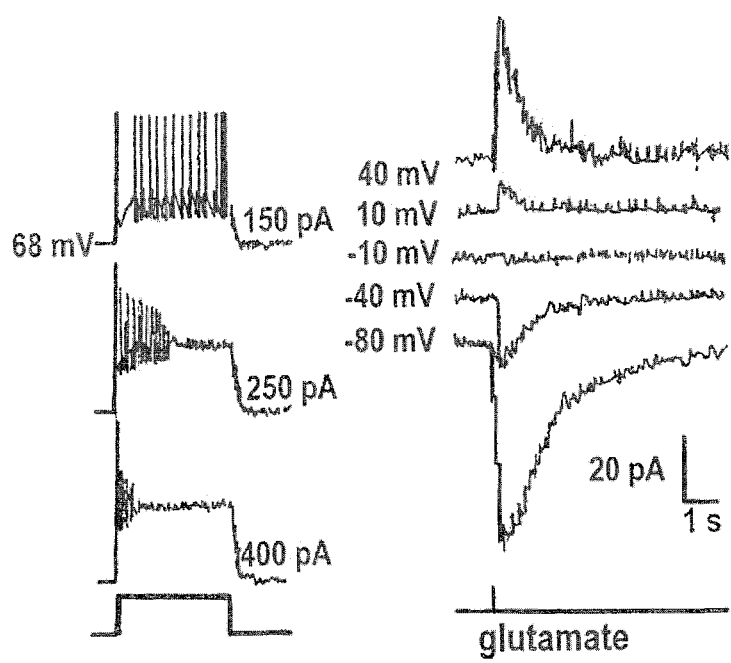
FIG. 4D are the patch-clamp recordings from RGCs maintained with DLK siRNA and/or sunitinib in response to depolarizing current (left) or glutamate iontophoresis (right). *$p<0.05$, #$p<0.005$; error bars, s.d.

To explore the role of DLK in mediating RGC death, immunopanned RGCs were transfected with DLK siRNA, or a nontargeting control, and survival over time followed. As predicted, DLK siRNA knocked down the level of DLK mRNA and protein and inhibited phosphorylation of JNK, a marker of activation of JNK downstream signaling (FIG. 4A). While nontargeting siRNA-transfected cells were dead by 72 hours, RGCs transfected with DLK siRNA survived for greater than 3 weeks (FIG. 4B). To determine whether the RGCs that are kept alive for extended periods with DLK siRNA or sunitinib treatment remain functional, patch-clamp recordings were performed at two weeks in culture. Consistent with persistent functionality, the RGCs conducted action potentials in response to depolarizing current and were responsive to exogenously applied glutamate. To test the role of DLK in vivo in response to axonal injury, mice carrying a foxed allele of $Dlk^1$ with capsid-modified adeno-associated virus 2 (AAV2) expressing the P1 bacteriophage recombinase Cre were intravitreally injected. After sufficient time for Cre-mediated deletion of Dlk, eyes were subjected to optic nerve crush. Compared to either $Dlk^{+/+}$ mice injected with AAV2-Cre or $Dlk^{fl/fl}$ mice in the absence of Cre, $Dlk^{fl/fl}$ mice injected with AAV2-Cre had a 75% reduction in RGC loss (FIGS. 4C and 4D).

Figure 5A:
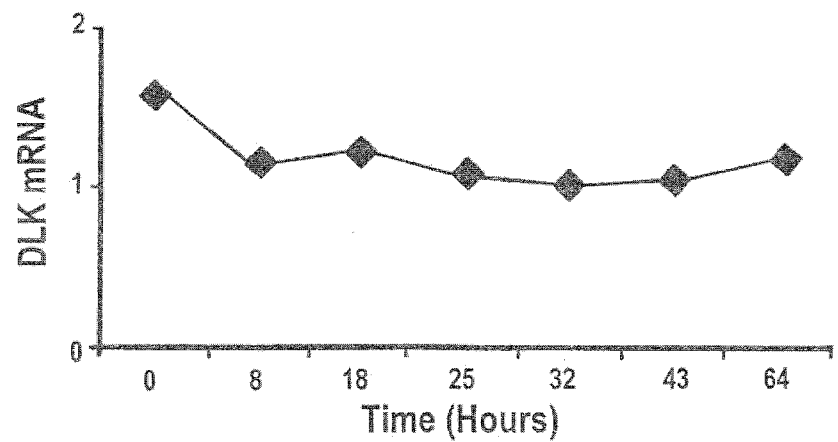
FIG. 5A is a graph showing DLK protein is upregulated in RGCs in response to injury, showing levels of DLK mRNA normalized to GAPDH, after various times in culture.

As DLK appears to be a critical mediator of RGC cell death in vitro and in vivo, the mechanism of DLK regulation was examined. Surprisingly, and unlike other members of the JNK cascade, DLK protein is undetectable in uninjured RGCs both in vitro and in vivo (FIG. 5A). However, after immunopanning in vitro (when RGCs are necessarily axotomized and injured), optic nerve crush, or transection in vivo, there is a robust upregulation of DLK protein). In contrast, Dlk transcript levels remained relatively constant after injury (FIG. 5A), indicating increased translation and/or decreased protein turnover as the mechanism mediating DLK upregulation.

Figure 5B:
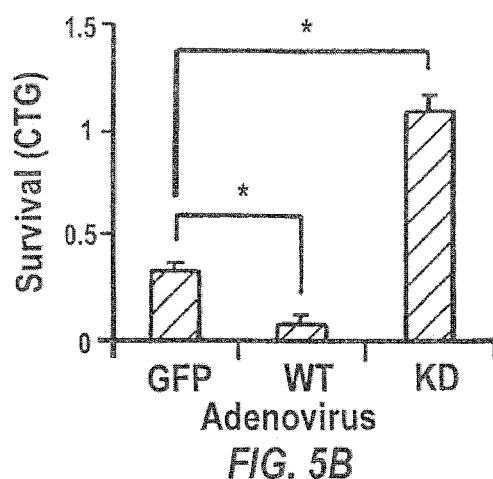
FIG. 5B is a graph of survival, measured by CellTiter-Glo (CTG) luminescence, of immunopanned RGCs 48 hours after transduction with adenovirus (MOI 1000) expressing wildtype (WT) or kinase-dead (KD) DLK. *$p<0.05$; error bars, s.d.

To directly test the hypothesis that increased DLK protein can trigger RGC cell death, adenovirus was used to overexpress GFP, DLK or a kinase-dead (KD) version of DLK (K185R). Primary RGCs were infected and survival measured 48 hours later. Consistent with the model, wildtype DLK overexpression hastened cell death, while overexpression of K185R DLK functioned as a dominant-negative, as assessed by JNK phosphorylation, and actually increased survival (FIG. 5B).

Given that both sunitinib treatment and DLK knockdown promote RGC survival, sunitinib's neuroprotective activity was mediated, at least in part, by DLK pathway inhibition. To assess sunitinib's effect on DLK signaling in RGCs, immunopanned cells were cultured in the presence of increasing amounts of sunitinib. The same concentrations that increase RGC survival caused a decrease in the phosphorylation of targets downstream of DLK, including MKK7 and JNK.

Figure 6A:
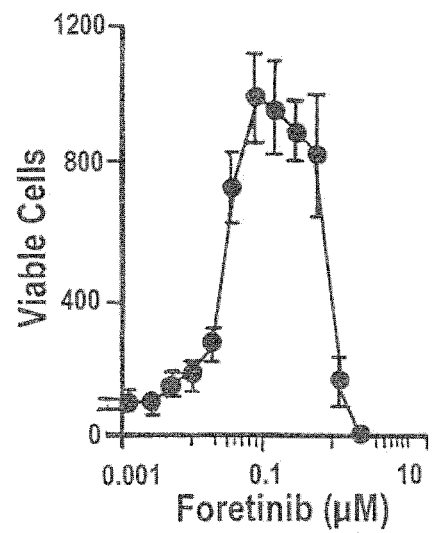
FIGS. 6A-6G are graphs of survival of immunopanned RGCs, treated with increasing doses of the indicated DLK inhibitors: foretinib, lestaurtinib, tozasertib, crizotinib, KW-2449, axitinib, and bosutinib, after 72 hours in culture.
Figure 6B:
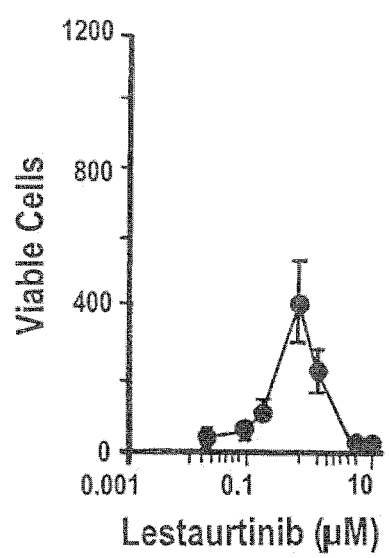
Figure 6C:
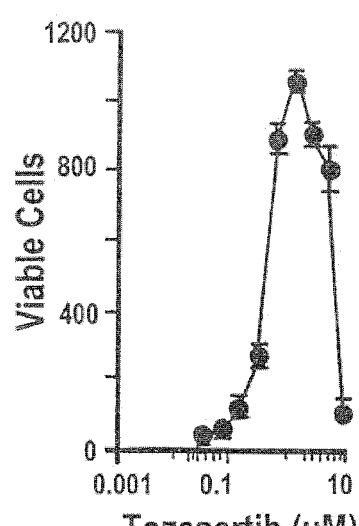
Figure 6D:
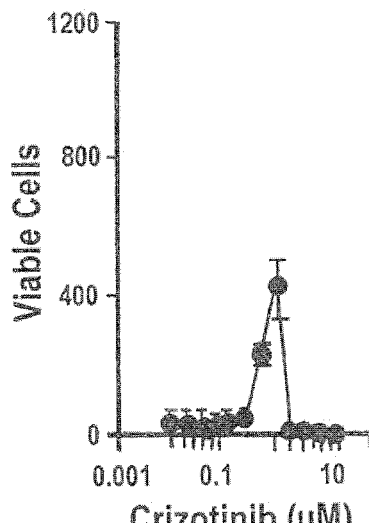
Figure 6E:
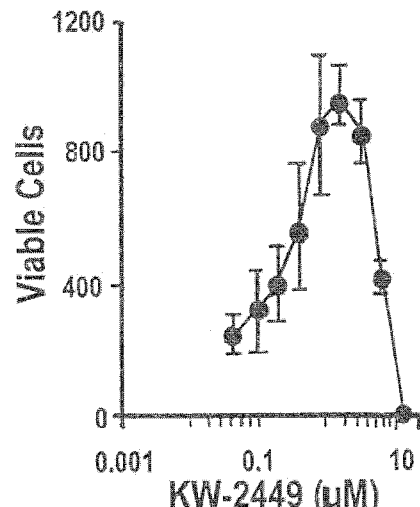
Figure 6F:
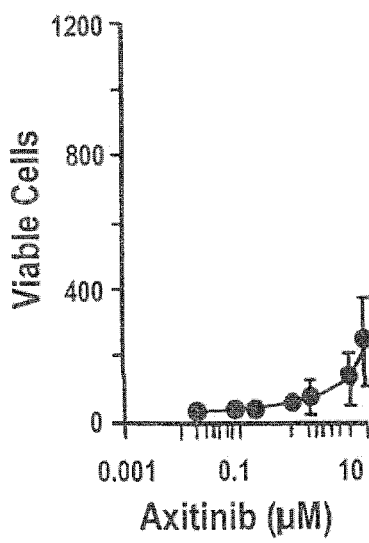
Figure 6G:
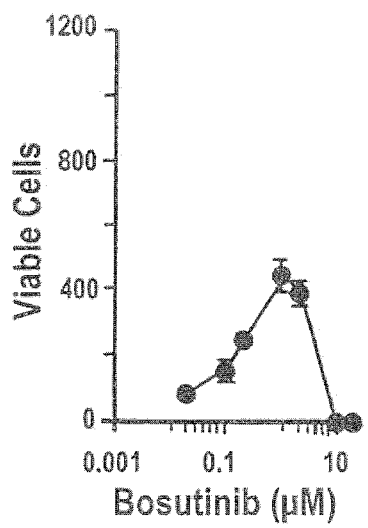
Figure 6H:
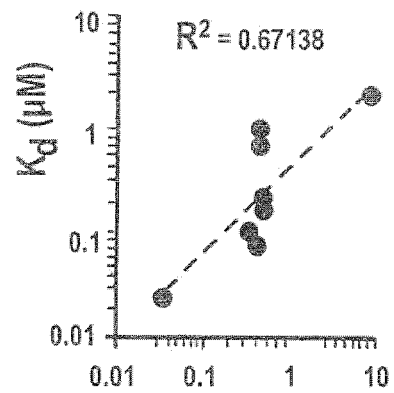
FIG. 6H is a graph of the relationship between the biochemical $K_d$ (ability of the inhibitor to bind purified DLK) and the cellular $ED_{50}$.
Figure 6I:
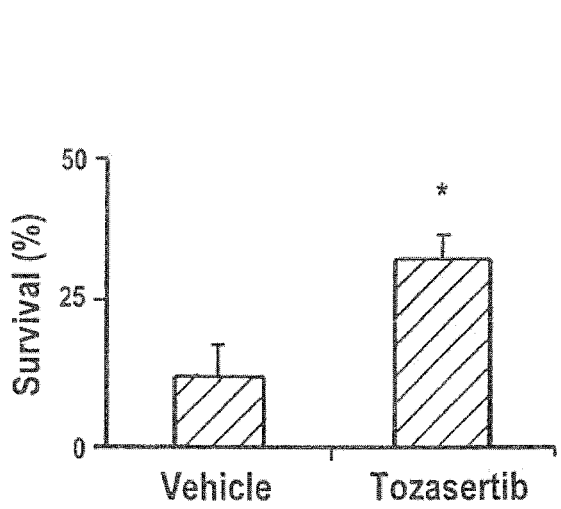
FIG. 6I is a graph of survival showing Tozasertib protects RGC axons from glaucomatous injury in rats.
Figure 6J:
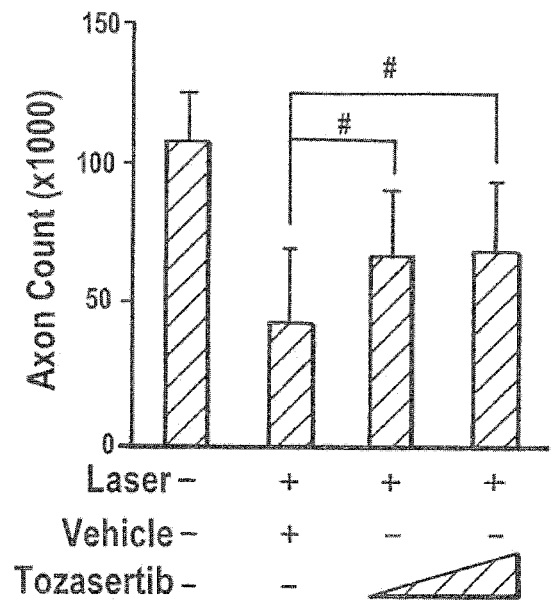
FIG. 6J is a graph of optic nerve axon counts following laser-induced ocular hypertension in rats pretreated with intravitreal drug-eluting microspheres containing vehicle (n=29), 82 ng (n=22) or 275 ng (n=21) tozasertib. Fellow eyes (n=157) shown for comparison. #$p<0.005$; error bars, s.d.

SR8165, a sunitinib analog with a widened therapeutic window, reduced DLK toxicity. Nine other compounds reported to bind DLK (axitinib, bosutinib, neratininb, crizotinib, tozasertib, lestautinib, foretinib, TAE-684 and KW-2449) were tested. Except for neratinib and TAE-684, which were limited by toxicity at nanomolar doses, the remaining kinase inhibitors all promoted the survival of primary RGCs in culture, with neuroprotective doses that roughly correlated with their biochemical affinity for purified DLK (FIGS. 6A-6H). To confirm these findings in vivo, intravitreal tozasertib in a slow release formulation was tested, and found that it protected RGCs in both the optic nerve transection and glaucoma models (FIGS. 6I and 6J).

The high-throughput screening identified sunitinib as a novel neuroprotective agent capable of promoting RGC survival in vitro and in vivo, including in a rodent model of glaucoma. Although initially a paradoxical finding, given the drug's inhibition of growth receptor signaling and stimulation of apoptosis, the finding that sunitinib's neuroprotective activity is likely mediated through inhibition of JNK signaling, via the DLK pathway, provides a mechanistic explanation for its neuroprotective activity. These results establish a therapeutic strategy for the treatment of glaucoma and related optic neuropathies, and may also have relevance to other CNS neurodegenerations.

Modifications and variations of the sunitinib formulations and methods of use thereof will be apparent to those of skill in the art and are intended to come within the scope of the appended claims.

---

---

We claim:

1. A method of reducing neuronal damage in the eye comprising administering an inhibitor of dual-leucine zipper kinase (DLK) in an amount effective to decrease or inhibit phosphorylation of c-Jun N-terminal kinases (JNK), in a sustained release formulation releasing inhibitor over a period of time of at least 30 days,
   wherein the inhibitor is selected from the group consisting of axitinib, bosutinib, neratinib, crizotinib, tozasertib, lestautinib, foretinib, TAE-684, KW-2449, and
   a compound of formula (1):

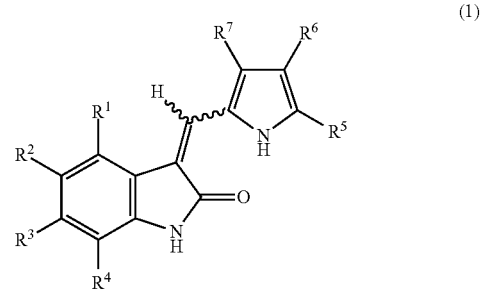

(1)

wherein
   $R^1$ is selected from the group consisting of hydrogen, halo, alkyl, cyclkoalkyl, aryl, heteroaryl, heteroalicyclic, hydroxy, alkoxy, —(CO)$R^{15}$, —NR$^{13}$R$^{14}$, —(CH$_2$),R$^{16}$ and —C(O)NR$^8$R$^9$;
   $R^2$ is selected from the group consisting of hydrogen, halo, alkyl, trihalomethyl, hydroxy, alkoxy, cyano, —NR$^{13}$R$^{14}$, —NR$^{13}$C(O)R$^{14}$, —C(O)R$^{15}$, aryl, heteroaryl, —S(O)$_2$NR$^{13}$R$^{14}$ and —SO$_2$R$^{20}$ (wherein R$^{20}$ is alkyl, aryl, aralkyl, heteroaryl and heteroaralkyl);

R³ is selected from the group consisting of hydrogen, halogen, alkyl, trihalomethyl, hydroxy, alkoxy, —(CO)R¹⁵, —NR¹³R¹⁴, aryl, heteroaryl, —NR¹³S(O)₂R¹⁴, —S(O)₂NR¹³R¹⁴, —NR¹³C(O)R¹⁴, —NR¹³C(O)OR¹⁴ and —SO₂R²⁰ (wherein R²⁰ is alkyl, aryl, aralkyl, heteroaryl and heteroaralkyl);

R⁴ is selected from the group consisting of hydrogen, halogen, alkyl, hydroxy, alkoxy and —NR¹³R¹⁴;

R⁵ is selected from the group consisting of hydrogen, alkyl and —C(O)R¹⁰;

R⁶ is selected from the group consisting of hydrogen, alkyl and —C(O)R¹⁰;

R⁷ is selected from the group consisting of hydrogen, alkyl, aryl, heteroaryl, —C(O)R¹⁷ and —C(O)R¹⁰; or R⁶ and R⁷ may combine to form a group selected from the group consisting of —(CH₂)₄—, —(CH₂)₅— and —(CH₂)₆—; with the proviso that at least one of R⁵, R⁶ or R⁷ must be —C(O)R¹⁰;

R⁸ and R⁹ are independently selected from the group consisting of hydrogen, alkyl and aryl;

R¹⁰ is selected from the group consisting of hydroxy, alkoxy, aryloxy, —N(R¹¹)(CH₂)ₙR¹², and —NR¹³R¹⁴;

R¹¹ is selected from the group consisting of hydrogen and alkyl;

R¹² is selected from the group consisting of —NR¹³R¹⁴, hydroxy, —C(O)R¹⁵, aryl, heteroaryl, —N⁺(O⁻)R¹³R¹⁴, —N(OH)R¹³, and —NHC(O)Rᵃ (wherein Rᵃ is unsubstituted alkyl, haloalkyl, or aralkyl);

R¹³ and R¹⁴ are independently selected from the group consisting of hydrogen, alkyl, cyanoalkyl, cycloalkyl, aryl and heteroaryl; or R¹³ and R¹⁴ may combine to form a heterocyclo group;

R¹⁵ is selected from the group consisting of hydrogen, hydroxy, alkoxy and aryloxy;

R¹⁶ is selected from the group consisting of hydroxy, —C(O)R¹⁵, —NR¹³R¹⁴ and —C(O)NR¹³R¹⁴;

R¹⁷ is selected from the group consisting of alkyl, cycloalkyl, aryl and heteroaryl;

R²⁰ is alkyl, aryl, aralkyl or heteroaryl; and n and r are independently 1, 2, 3, or 4;

or a pharmaceutically acceptable salt thereof, wherein the sustained release formulation comprises polymeric particles formed of a blend of a hydrophobic polymer selected from the group consisting of polyhydroxyesters, polycaprolactone, polyorthoesters, polyanhydrides, and copolymers thereof, and an amphipathic polymer comprising a polyethylene, the polymeric particles containing more than 10% by weight of inhibitor.

2. The method of claim 1 wherein the inhibitor is sunitinib or a pharmaceutically acceptable salt thereof.

3. The method of claim 1 wherein the inhibitor is a sustained release formulation releasing over a period of at least 45 days.

4. The method of claim 1 wherein the formulation is made by increasing the alkalinity of the inhibitor in a solution at the time of encapsulation or incorporation into the polymeric particles.

5. The method of claim 4 wherein the inhibitor is formulated into polymeric nano or microparticles.

6. The method of claim 5 wherein the inhibitor is incorporated into the polymer at a loading greater than 10% or 15% by weight.

7. The method of claim 1 wherein particles comprising the inhibitor are incorporated into a polymeric implant.

8. The method of claim 1 wherein the formulation comprises a polymer selected from the group consisting of poly(hydroxy acids), copolymers and blends thereof.

9. The method of claim 1, wherein the formulation is applied to or into the eye.

10. The method of claim 9 wherein the individual to be treated has a disease or disorder having a risk of neuronal damage.

11. The method of claim 2 wherein the inhibitor is sunitinib or a pharmaceutically acceptable salt thereof.

12. The method of claim 8 wherein the formulation comprises a polymer selected from the group consisting of poly(lactic acid), poly(glycolic acid), poly(lactic acid-co-glycolic acid), poly(lactide), poly(glycolide), poly(lactide-co-glycolide), poly(ethylene glycol), ppoly(ethylene oxide), copolymers and blends thereof.

13. The method of claim 1, wherein the inhibitor of DLK reduces the mRNA level of DLK.

14. The method of claim 2, wherein the inhibitor is sunitinib malate.

* * * * *

UNITED STATES PATENT AND TRADEMARK OFFICE
CERTIFICATE OF CORRECTION

PATENT NO. : 10,525,034 B2
APPLICATION NO. : 15/536272
DATED : January 7, 2020
INVENTOR(S) : Fu et al.

It is certified that error appears in the above-identified patent and that said Letters Patent is hereby corrected as shown below:

In the Specification

Column 1, Line 17, please insert the following paragraph:
--STATEMENT REGARDING FEDERALLY SPONSORED RESEARCH
This invention was made with government support under EY023754 and EY026578 awarded by the National Institutes of Health. The government has certain rights in the invention.--

Signed and Sealed this
Second Day of June, 2020

Andrei Iancu
*Director of the United States Patent and Trademark Office*